(12) United States Patent
Kyutoku et al.

(10) Patent No.: US 9,913,886 B2
(45) Date of Patent: Mar. 13, 2018

(54) DNA VACCINE CONTAINING SPECIFIC EPITOPE OF APOLIPOPROTEIN (A)

(71) Applicant: AnGes, Inc., Ibaraki-shi, Osaka (JP)

(72) Inventors: Mariko Kyutoku, Ibaraki (JP);
Hironori Nakagami, Ibaraki (JP);
Hiroshi Koriyama, Ibaraki (JP);
Futoshi Nakagami, Ibaraki (JP);
Ryuichi Morishita, Ibaraki (JP)

(73) Assignee: AnGes, Inc., Osaka (JP)

( * ) Notice: Subject to any disclaimer, the term of this patent is extended or adjusted under 35 U.S.C. 154(b) by 0 days.

(21) Appl. No.: 15/201,029

(22) Filed: Jul. 1, 2016

(65) Prior Publication Data

US 2016/0303211 A1 Oct. 20, 2016

Related U.S. Application Data

(62) Division of application No. 14/032,804, filed on Sep. 20, 2013, now abandoned.

(30) Foreign Application Priority Data

Sep. 21, 2012 (JP) ................. 2012-208796

(51) Int. Cl.
*C12N 7/00* (2006.01)
*A61K 39/29* (2006.01)
*A61K 39/00* (2006.01)
*C12N 15/85* (2006.01)

(52) U.S. Cl.
CPC ........ *A61K 39/0012* (2013.01); *A61K 39/292* (2013.01); *C12N 7/00* (2013.01); *C12N 15/85* (2013.01); *A61K 2039/53* (2013.01); *A61K 2039/545* (2013.01); *A61K 2039/575* (2013.01); *A61K 2039/58* (2013.01); *C12N 2730/10142* (2013.01); *C12N 2730/10143* (2013.01); *C12N 2730/10171* (2013.01)

(58) Field of Classification Search
None
See application file for complete search history.

(56) References Cited

U.S. PATENT DOCUMENTS

| | | | |
|---|---|---|---|
| 5,278,189 A * | 1/1994 | Rath | A61K 31/375 514/356 |
| 5,721,138 A | 2/1998 | Lawn | |
| 5,733,549 A | 3/1998 | Yamada et al. | |
| 6,512,161 B1 | 1/2003 | Rouy et al. | |
| 6,713,301 B1 | 3/2004 | Wang | |
| 7,745,606 B2 | 6/2010 | Dina et al. | |
| 2003/0157479 A1 | 8/2003 | Bachmann et al. | |
| 2003/0175296 A1 | 9/2003 | Brown et al. | |
| 2012/0157513 A1 | 6/2012 | Li et al. | |
| 2014/0086944 A1 | 3/2014 | Kyutoku et al. | |
| 2014/0099335 A1 | 4/2014 | Morishita et al. | |

FOREIGN PATENT DOCUMENTS

| | | |
|---|---|---|
| CN | 1201819 C | 5/2005 |
| CN | 1706502 A | 12/2005 |
| CN | 1896094 A | 1/2007 |
| CN | 101015689 A | 8/2007 |
| CN | 102247604 A | 11/2011 |
| EP | 0 421 635 A1 | 4/1991 |
| JP | 3228737 B2 | 9/2001 |
| JP | 2002-500039 A | 1/2002 |
| JP | 2005-514333 A | 5/2005 |
| WO | WO 1999/015655 A1 | 4/1999 |
| WO | WO 2001/098333 A2 | 12/2001 |
| WO | WO 2003/031466 A2 | 4/2003 |

OTHER PUBLICATIONS

Saeedi et al., Clinical Diabetes and Endocrinology, 2(7): 1-6, 2016.*
Fredrikson et al., J. of Internal Medicine, 264: 563-570, 2008.*
Wigren et al., Journal of Internal Medicine, 269: 546-556 (2010).
Ambuhl et al., Journal of Hypertension, 25(1): 63-72 (2007).
Berg, Kare, Acta Pathologica Microbiologica Scandinavica, 59: 369-382 (1963).
Brown et al., New England Journal of Medicine, 323: 1289-1298 (1990).
Clarke et al., Nature, 330: 381-384 (1987).
Do et al., Expert Opin. Biol. Ther., 10(7): 1077-1087 (2010).
Eaton et al., Proc. Natl. Acad. Sci. USA, 84: 3224-3228 (1987).
Ishii et al., Nature, 451: 725-729 (2008).
Koriyama et al., "Long Term Blood Pressure Reduction by Angiotensin II DNA Vaccine in Spontaneously Hypertensive Rats Model," abstract of Presentation 16969 at American Heart Association Symposium at Dallas, Texas (Nov. 18, 2013).
Kyutoku et al., "The Challenge for Apolipoprotein(a) DNA Vaccine as a New Therapeutic Strategy for Patients with Elevated Serum Lipoprotein(a) Level," Japan Atherosclerosis Society, Program & Proceedings, Abstract for Poster Session HS-7, pp. 59-60 and 197 (Jul. 19, 2012).
Kyutoku et al., "The Challenge for Apolipoprotein(a) DNA Vaccine as a New Therapeutic Strategy for Patients with Elevated Serum Lipoprotein(a) Level," The 44th Annual Scientific Meeting of the Japan Atherosclerosis Society, Poster Session HS-7 at the Hilton Fukuoka Sea Hawk Hotel in Fukuoka, Japan (Jul. 19, 2012).
Mao et al., Vaccine, 24: 4942-4950 (2006).
Marshall et al., Journal of Leukocyte Biology, 82: 497-508 (2007).
McLean et al., Nature, 330: 132-137 (1987).
Miles et al., Nature, 339(6222): 301-303 (1989).
Morgan et al., Nature, 408: 982-985 (2000).
Nakagami et al., Atherosclerosis, 211: 41-47 (2010).
Nakagami et al., International Heart Journal, 55(2): 96-100 (2014).
Nakagami et al., Journal of Cardiac Failure, 20(10), S151, Abstract O-037 (2014).

(Continued)

*Primary Examiner* — Thaian N Ton
(74) *Attorney, Agent, or Firm* — Leydig, Voit & Mayer, Ltd.

(57) ABSTRACT

The present invention provides an agent for the treatment or prophylaxis of arteriosclerosis comprising an expression vector encoding a chimeric Hepatitis B virus core antigen polypeptide inserted with an amino acid sequence containing a specific epitope of apolipoprotein (a), wherein the amino acid sequence containing the specific epitope is inserted between the amino acid residues 80 and 81 of the hepatitis B virus core antigen polypeptide.

22 Claims, 6 Drawing Sheets

(56) References Cited

OTHER PUBLICATIONS

Nakagami et al., "Development of dyslipidemia DNA vaccine system for Lipoprotein(a)," Japan Society of Gene Therapy, 18th Annual Meeting Program, Program, Identity of Poster Session PO-78, pp. 21-23 [obtained from internet URL: http://jsgt.jp] (Jun. 28-30, 2012).

Nakagami et al., "Development of dyslipidemia DNA vaccine system for Lipoprotein(a)," Japan Society of Gene Therapy, 18th Annual Meeting Program, Program & Abstracts, Abstract for Poster Session PO-78, pp. 21-22 and 175 (Jun. 28-30, 2012).

Nakagami et al., "Development of dyslipidemia DNA vaccine system for Lipoprotein(a)," The 18th Annual Meeting of the Japan Society of Gene Therapy, Poster Session PO-78 at the Hotel Kumamoto Terrsa in Kumamoto, Japan (Jun. 28-30, 2012).

Scanu et al., *Journal of Clinical Investigation*, 85: 1709-1715 (1990).

Schenk, Dale, *Nat. Rev. Neuroscience*, 3: 824-828 (2002).

Schodel et al., *Journal of Virology*, 66(1) 106-114 (1992).

Schodel et al., *The Journal of Experimental Medicine*, 180: 1037-1046 (1994).

Taylor et al., *The New England Journal of Medicine*, 361: 2113-2122 (2009).

Tissot et al., *The Lancet*, 371: 821-827 (2008).

Whitacre et al., *Expert Rev. Vaccines*, 8(11): 1565-1573 (2009).

Yamada et al., *Clinica Chimica Acta*, 287: 29-43 (1999).

Chinese Patent Office, Office Action in Chinese Patent Application No. 201280027097.4 (dated Oct. 10, 2014).

European Patent Office, Extended European Search Report in European Patent Application No. 12771621.5 (dated Dec. 22, 2014).

Japanese Patent Office, International Search Report in International Patent Application No. PCT/JP2012/060099 (dated Jul. 17, 2012).

Cho et al., *Journal of Biological Chemistry*, 283(45): 30503-30512 (2008).

* cited by examiner

SEQUENCE LISTING

<160> NUMBER OF SEQ ID NOS: 17

<210> SEQ ID NO 1
<211> LENGTH: 12
<212> TYPE: PRT
<213> ORGANISM: Mus musculus

<400> SEQUENCE: 1

Glu Ala Pro Ser Glu Gln Ala Pro Thr Glu Gln Arg
1               5                   10

<210> SEQ ID NO 2
<211> LENGTH: 2040
<212> TYPE: PRT
<213> ORGANISM: Homo sapiens

<400> SEQUENCE: 2

Met Glu His Lys Glu Val Val Leu Leu Leu Leu Phe Leu Lys Ser
1               5                   10                  15

Ala Ala Pro Glu Gln Ser His Val Val Gln Asp Cys Tyr His Gly Asp
                20                  25                  30

Gly Gln Ser Tyr Arg Gly Thr Tyr Ser Thr Thr Val Thr Gly Arg Thr
                35                  40                  45

Cys Gln Ala Trp Ser Ser Met Thr Pro His Gln His Asn Arg Thr Thr
            50                  55                  60

Glu Asn Tyr Pro Asn Ala Gly Leu Ile Met Asn Tyr Cys Arg Asn Pro
65              70                  75                  80

Asp Ala Val Ala Ala Pro Tyr Cys Tyr Thr Arg Asp Pro Gly Val Arg
                85                  90                  95

Trp Glu Tyr Cys Asn Leu Thr Gln Cys Ser Asp Ala Glu Gly Thr Ala
            100                 105                 110

Val Ala Pro Pro Thr Val Thr Pro Val Pro Ser Leu Glu Ala Pro Ser
                115                 120                 125

Glu Gln Ala Pro Thr Glu Gln Arg Pro Gly Val Gln Glu Cys Tyr His
                130                 135                 140

Gly Asn Gly Gln Ser Tyr Arg Gly Thr Tyr Ser Thr Thr Val Thr Gly
145             150                 155                 160

Arg Thr Cys Gln Ala Trp Ser Ser Met Thr Pro His Ser His Ser Arg
                165                 170                 175

Thr Pro Glu Tyr Tyr Pro Asn Ala Gly Leu Ile Met Asn Tyr Cys Arg
                180                 185                 190

Asn Pro Asp Ala Val Ala Ala Pro Tyr Cys Tyr Thr Arg Asp Pro Gly
            195                 200                 205

Val Arg Trp Glu Tyr Cys Asn Leu Thr Gln Cys Ser Asp Ala Glu Gly
        210                 215                 220

Thr Ala Val Ala Pro Pro Thr Val Thr Pro Val Pro Ser Leu Glu Ala
225                 230                 235                 240

Pro Ser Glu Gln Ala Pro Thr Glu Gln Arg Pro Gly Val Gln Glu Cys
                245                 250                 255

Tyr His Gly Asn Gly Gln Ser Tyr Arg Gly Thr Tyr Ser Thr Thr Val
                260                 265                 270

Thr Gly Arg Thr Cys Gln Ala Trp Ser Ser Met Thr Pro His Ser His
            275                 280                 285

Ser Arg Thr Pro Glu Tyr Tyr Pro Asn Ala Gly Leu Ile Met Asn Tyr
        290                 295                 300

Cys Arg Asn Pro Asp Ala Val Ala Ala Pro Tyr Cys Tyr Thr Arg Asp

```
            305                 310                 315                 320
Pro Gly Val Arg Trp Glu Tyr Cys Asn Leu Thr Gln Cys Ser Asp Ala
                325                 330                 335
Glu Gly Thr Ala Val Ala Pro Pro Thr Val Thr Pro Val Pro Ser Leu
                340                 345                 350
Glu Ala Pro Ser Glu Gln Ala Pro Thr Glu Gln Arg Pro Gly Val Gln
                355                 360                 365
Glu Cys Tyr His Gly Asn Gly Gln Ser Tyr Arg Gly Thr Tyr Ser Thr
                370                 375                 380
Thr Val Thr Gly Arg Thr Cys Gln Ala Trp Ser Ser Met Thr Pro His
385                 390                 395                 400
Ser His Ser Arg Thr Pro Glu Tyr Tyr Pro Asn Ala Gly Leu Ile Met
                405                 410                 415
Asn Tyr Cys Arg Asn Pro Asp Ala Val Ala Ala Pro Tyr Cys Tyr Thr
                420                 425                 430
Arg Asp Pro Gly Val Arg Trp Glu Tyr Cys Asn Leu Thr Gln Cys Ser
                435                 440                 445
Asp Ala Glu Gly Thr Ala Val Ala Pro Pro Thr Val Thr Pro Val Pro
                450                 455                 460
Ser Leu Glu Ala Pro Ser Glu Gln Ala Pro Thr Glu Gln Arg Pro Gly
465                 470                 475                 480
Val Gln Glu Cys Tyr His Gly Asn Gly Gln Ser Tyr Arg Gly Thr Tyr
                485                 490                 495
Ser Thr Thr Val Thr Gly Arg Thr Cys Gln Ala Trp Ser Ser Met Thr
                500                 505                 510
Pro His Ser His Ser Arg Thr Pro Glu Tyr Tyr Pro Asn Ala Gly Leu
                515                 520                 525
Ile Met Asn Tyr Cys Arg Asn Pro Asp Ala Val Ala Ala Pro Tyr Cys
                530                 535                 540
Tyr Thr Arg Asp Pro Gly Val Arg Trp Glu Tyr Cys Asn Leu Thr Gln
545                 550                 555                 560
Cys Ser Asp Ala Glu Gly Thr Ala Val Ala Pro Pro Thr Val Thr Pro
                565                 570                 575
Val Pro Ser Leu Glu Ala Pro Ser Glu Gln Ala Pro Thr Glu Gln Arg
                580                 585                 590
Pro Gly Val Gln Glu Cys Tyr His Gly Asn Gly Gln Ser Tyr Arg Gly
                595                 600                 605
Thr Tyr Ser Thr Thr Val Thr Gly Arg Thr Cys Gln Ala Trp Ser Ser
                610                 615                 620
Met Thr Pro His Ser His Ser Arg Thr Pro Glu Tyr Tyr Pro Asn Ala
625                 630                 635                 640
Gly Leu Ile Met Asn Tyr Cys Arg Asn Pro Asp Ala Val Ala Ala Pro
                645                 650                 655
Tyr Cys Tyr Thr Arg Asp Pro Gly Val Arg Trp Glu Tyr Cys Asn Leu
                660                 665                 670
Thr Gln Cys Ser Asp Ala Glu Gly Thr Ala Val Ala Pro Pro Thr Val
                675                 680                 685
Thr Pro Val Pro Ser Leu Glu Ala Pro Ser Glu Gln Ala Pro Thr Glu
                690                 695                 700
Gln Arg Pro Gly Val Gln Glu Cys Tyr His Gly Asn Gly Gln Ser Tyr
705                 710                 715                 720
Arg Gly Thr Tyr Ser Thr Thr Val Thr Gly Arg Thr Cys Gln Ala Trp
                725                 730                 735
```

```
Ser Ser Met Thr Pro His Ser His Ser Arg Thr Pro Glu Tyr Tyr Pro
            740                 745                 750

Asn Ala Gly Leu Ile Met Asn Tyr Cys Arg Asn Pro Asp Ala Val Ala
            755                 760                 765

Ala Pro Tyr Cys Tyr Thr Arg Asp Pro Gly Val Arg Trp Glu Tyr Cys
            770                 775                 780

Asn Leu Thr Gln Cys Ser Asp Ala Glu Gly Thr Ala Val Ala Pro Pro
785                 790                 795                 800

Thr Val Thr Pro Val Pro Ser Leu Glu Ala Pro Ser Glu Gln Ala Pro
                805                 810                 815

Thr Glu Gln Arg Pro Gly Val Gln Glu Cys Tyr His Gly Asn Gly Gln
            820                 825                 830

Ser Tyr Arg Gly Thr Tyr Ser Thr Thr Val Thr Gly Arg Thr Cys Gln
            835                 840                 845

Ala Trp Ser Ser Met Thr Pro His Ser His Ser Arg Thr Pro Glu Tyr
            850                 855                 860

Tyr Pro Asn Ala Gly Leu Ile Met Asn Tyr Cys Arg Asn Pro Asp Pro
865                 870                 875                 880

Val Ala Ala Pro Tyr Cys Tyr Thr Arg Asp Pro Ser Val Arg Trp Glu
                885                 890                 895

Tyr Cys Asn Leu Thr Gln Cys Ser Asp Ala Glu Gly Thr Ala Val Ala
            900                 905                 910

Pro Pro Thr Ile Thr Pro Ile Pro Ser Leu Glu Ala Pro Ser Glu Gln
            915                 920                 925

Ala Pro Thr Glu Gln Arg Pro Gly Val Gln Glu Cys Tyr His Gly Asn
            930                 935                 940

Gly Gln Ser Tyr Gln Gly Thr Tyr Phe Ile Thr Val Thr Gly Arg Thr
945                 950                 955                 960

Cys Gln Ala Trp Ser Ser Met Thr Pro His Ser His Ser Arg Thr Pro
                965                 970                 975

Ala Tyr Tyr Pro Asn Ala Gly Leu Ile Lys Asn Tyr Cys Arg Asn Pro
            980                 985                 990

Asp Pro Val Ala Ala Pro Trp Cys Tyr Thr Thr Asp Pro Ser Val Arg
            995                 1000                1005

Trp Glu Tyr Cys Asn Leu Thr Arg Cys Ser Asp Ala Glu Trp Thr
        1010                1015                1020

Ala Phe Val Pro Pro Asn Val Ile Leu Ala Pro Ser Leu Glu Ala
        1025                1030                1035

Phe Phe Glu Gln Ala Leu Thr Glu Glu Thr Pro Gly Val Gln Asp
        1040                1045                1050

Cys Tyr Tyr His Tyr Gly Gln Ser Tyr Arg Gly Thr Tyr Ser Thr
        1055                1060                1065

Thr Val Thr Gly Arg Thr Cys Gln Ala Trp Ser Ser Met Thr Pro
        1070                1075                1080

His Gln His Ser Arg Thr Pro Glu Asn Tyr Pro Asn Ala Gly Leu
        1085                1090                1095

Thr Arg Asn Tyr Cys Arg Asn Pro Asp Ala Glu Ile Arg Pro Trp
        1100                1105                1110

Cys Tyr Thr Met Asp Pro Ser Val Arg Trp Glu Tyr Cys Asn Leu
        1115                1120                1125

Thr Gln Cys Leu Val Thr Glu Ser Ser Val Leu Ala Thr Leu Thr
        1130                1135                1140
```

```
Val Val Pro Asp Pro Ser Thr Glu Ala Ser Ser Glu Glu Ala Pro
    1145                1150                1155

Thr Glu Gln Ser Pro Gly Val Gln Asp Cys Tyr His Gly Asp Gly
    1160                1165                1170

Gln Ser Tyr Arg Gly Ser Phe Ser Thr Thr Val Thr Gly Arg Thr
    1175                1180                1185

Cys Gln Ser Trp Ser Ser Met Thr Pro His Trp His Gln Arg Thr
    1190                1195                1200

Thr Glu Tyr Tyr Pro Asn Gly Gly Leu Thr Arg Asn Tyr Cys Arg
    1205                1210                1215

Asn Pro Asp Ala Glu Ile Ser Pro Trp Cys Tyr Thr Met Asp Pro
    1220                1225                1230

Asn Val Arg Trp Glu Tyr Cys Asn Leu Thr Gln Cys Pro Val Thr
    1235                1240                1245

Glu Ser Ser Val Leu Ala Thr Ser Thr Ala Val Ser Glu Gln Ala
    1250                1255                1260

Pro Thr Glu Gln Ser Pro Thr Val Gln Asp Cys Tyr His Gly Asp
    1265                1270                1275

Gly Gln Ser Tyr Arg Gly Ser Phe Ser Thr Thr Val Thr Gly Arg
    1280                1285                1290

Thr Cys Gln Ser Trp Ser Ser Met Thr Pro His Trp His Gln Arg
    1295                1300                1305

Thr Thr Glu Tyr Tyr Pro Asn Gly Gly Leu Thr Arg Asn Tyr Cys
    1310                1315                1320

Arg Asn Pro Asp Ala Glu Ile Arg Pro Trp Cys Tyr Thr Met Asp
    1325                1330                1335

Pro Ser Val Arg Trp Glu Tyr Cys Asn Leu Thr Gln Cys Pro Val
    1340                1345                1350

Met Glu Ser Thr Leu Leu Thr Thr Pro Thr Val Val Pro Val Pro
    1355                1360                1365

Ser Thr Glu Leu Pro Ser Glu Ala Pro Thr Glu Asn Ser Thr
    1370                1375                1380

Gly Val Gln Asp Cys Tyr Arg Gly Asp Gly Gln Ser Tyr Arg Gly
    1385                1390                1395

Thr Leu Ser Thr Thr Ile Thr Gly Arg Thr Cys Gln Ser Trp Ser
    1400                1405                1410

Ser Met Thr Pro His Trp His Arg Arg Ile Pro Leu Tyr Tyr Pro
    1415                1420                1425

Asn Ala Gly Leu Thr Arg Asn Tyr Cys Arg Asn Pro Asp Ala Glu
    1430                1435                1440

Ile Arg Pro Trp Cys Tyr Thr Met Asp Pro Ser Val Arg Trp Glu
    1445                1450                1455

Tyr Cys Asn Leu Thr Arg Cys Pro Val Thr Glu Ser Ser Val Leu
    1460                1465                1470

Thr Thr Pro Thr Val Ala Pro Val Pro Ser Thr Glu Ala Pro Ser
    1475                1480                1485

Glu Gln Ala Pro Pro Glu Lys Ser Pro Val Val Gln Asp Cys Tyr
    1490                1495                1500

His Gly Asp Gly Arg Ser Tyr Arg Gly Ile Ser Ser Thr Thr Val
    1505                1510                1515

Thr Gly Arg Thr Cys Gln Ser Trp Ser Ser Met Ile Pro His Trp
    1520                1525                1530

His Gln Arg Thr Pro Glu Asn Tyr Pro Asn Ala Gly Leu Thr Glu
```

-continued

```
            1535                1540                1545

Asn Tyr Cys Arg Asn Pro Asp Ser Gly Lys Gln Pro Trp Cys Tyr
            1550                1555                1560

Thr Thr Asp Pro Cys Val Arg Trp Glu Tyr Cys Asn Leu Thr Gln
            1565                1570                1575

Cys Ser Glu Thr Glu Ser Gly Val Leu Glu Thr Pro Thr Val Val
            1580                1585                1590

Pro Val Pro Ser Met Glu Ala His Ser Glu Ala Ala Pro Thr Glu
            1595                1600                1605

Gln Thr Pro Val Val Arg Gln Cys Tyr His Gly Asn Gly Gln Ser
            1610                1615                1620

Tyr Arg Gly Thr Phe Ser Thr Thr Val Thr Gly Arg Thr Cys Gln
            1625                1630                1635

Ser Trp Ser Ser Met Thr Pro His Arg His Gln Arg Thr Pro Glu
            1640                1645                1650

Asn Tyr Pro Asn Asp Gly Leu Thr Met Asn Tyr Cys Arg Asn Pro
            1655                1660                1665

Asp Ala Asp Thr Gly Pro Trp Cys Phe Thr Met Asp Pro Ser Ile
            1670                1675                1680

Arg Trp Glu Tyr Cys Asn Leu Thr Arg Cys Ser Asp Thr Glu Gly
            1685                1690                1695

Thr Val Val Ala Pro Pro Thr Val Ile Gln Val Pro Ser Leu Gly
            1700                1705                1710

Pro Pro Ser Glu Gln Asp Cys Met Phe Gly Asn Gly Lys Gly Tyr
            1715                1720                1725

Arg Gly Lys Lys Ala Thr Thr Val Thr Gly Thr Pro Cys Gln Glu
            1730                1735                1740

Trp Ala Ala Gln Glu Pro His Arg His Ser Thr Phe Ile Pro Gly
            1745                1750                1755

Thr Asn Lys Trp Ala Gly Leu Glu Lys Asn Tyr Cys Arg Asn Pro
            1760                1765                1770

Asp Gly Asp Ile Asn Gly Pro Trp Cys Tyr Thr Met Asn Pro Arg
            1775                1780                1785

Lys Leu Phe Asp Tyr Cys Asp Ile Pro Leu Cys Ala Ser Ser Ser
            1790                1795                1800

Phe Asp Cys Gly Lys Pro Gln Val Glu Pro Lys Lys Cys Pro Gly
            1805                1810                1815

Ser Ile Val Gly Gly Cys Val Ala His Pro His Ser Trp Pro Trp
            1820                1825                1830

Gln Val Ser Leu Arg Thr Arg Phe Gly Lys His Phe Cys Gly Gly
            1835                1840                1845

Thr Leu Ile Ser Pro Glu Trp Val Leu Thr Ala Ala His Cys Leu
            1850                1855                1860

Lys Lys Ser Ser Arg Pro Ser Ser Tyr Lys Val Ile Leu Gly Ala
            1865                1870                1875

His Gln Glu Val Asn Leu Glu Ser His Val Gln Glu Ile Glu Val
            1880                1885                1890

Ser Arg Leu Phe Leu Glu Pro Thr Gln Ala Asp Ile Ala Leu Leu
            1895                1900                1905

Lys Leu Ser Arg Pro Ala Val Ile Thr Asp Lys Val Met Pro Ala
            1910                1915                1920

Cys Leu Pro Ser Pro Asp Tyr Met Val Thr Ala Arg Thr Glu Cys
            1925                1930                1935
```

```
Tyr Ile Thr Gly Trp Gly Glu Thr Gln Gly Thr Phe Gly Thr Gly
    1940            1945                1950

Leu Leu Lys Glu Ala Gln Leu Leu Val Ile Glu Asn Glu Val Cys
    1955            1960                1965

Asn His Tyr Lys Tyr Ile Cys Ala Glu His Leu Ala Arg Gly Thr
    1970            1975                1980

Asp Ser Cys Gln Gly Asp Ser Gly Gly Pro Leu Val Cys Phe Glu
    1985            1990                1995

Lys Asp Lys Tyr Ile Leu Gln Gly Val Thr Ser Trp Gly Leu Gly
    2000            2005                2010

Cys Ala Arg Pro Asn Lys Pro Gly Val Tyr Ala Arg Val Ser Arg
    2015            2020                2025

Phe Val Thr Trp Ile Glu Gly Met Met Arg Asn Asn
    2030            2035                2040

<210> SEQ ID NO 3
<211> LENGTH: 556
<212> TYPE: DNA
<213> ORGANISM: Hepatitis B virus
<220> FEATURE:
<221> NAME/KEY: CDS
<222> LOCATION: (2)..(553)

<400> SEQUENCE: 3 c atg gat atc gat cct tat aaa gaa ttc gga gct act gtg gag tta ctc       49
  Met Asp Ile Asp Pro Tyr Lys Glu Phe Gly Ala Thr Val Glu Leu Leu
  1               5                  10                 15 tcg ttt ctc ccg agt gac ttt ttt cct tca gta cga gat ctt ctg gat        97
Ser Phe Leu Pro Ser Asp Phe Phe Pro Ser Val Arg Asp Leu Leu Asp
            20                  25                  30 acc gcc agc gcg ctg tat cgg gaa gcc ttg gag tct cct gag cac tgc       145
Thr Ala Ser Ala Leu Tyr Arg Glu Ala Leu Glu Ser Pro Glu His Cys
        35                  40                  45 agc cct cac cat act gcc ctc agg caa gca att ctt tgc tgg ggg gag       193
Ser Pro His His Thr Ala Leu Arg Gln Ala Ile Leu Cys Trp Gly Glu
    50                  55                  60 ctc atg act ctg gcc acg tgg gtg ggt gtt aac ttg gaa gat cca gct       241
Leu Met Thr Leu Ala Thr Trp Val Gly Val Asn Leu Glu Asp Pro Ala
65                  70                  75                  80 agc agg gac ctg gta gtc agt tat gtc aac act aat atg ggt tta aag       289
Ser Arg Asp Leu Val Val Ser Tyr Val Asn Thr Asn Met Gly Leu Lys
                85                  90                  95 ttc agg caa ctc ttg tgg ttt cac att agc tgc ctc act ttc ggc cga       337
Phe Arg Gln Leu Leu Trp Phe His Ile Ser Cys Leu Thr Phe Gly Arg
            100                 105                 110 gaa aca gtt cta gaa tat ttg gtg tct ttc gga gtg tgg atc cgc act       385
Glu Thr Val Leu Glu Tyr Leu Val Ser Phe Gly Val Trp Ile Arg Thr
        115                 120                 125 cct cca gct tat agg cct ccg aat gcc cct atc ctg tcg aca ctc ccg       433
Pro Pro Ala Tyr Arg Pro Pro Asn Ala Pro Ile Leu Ser Thr Leu Pro
    130                 135                 140 gag act act gtt gtt aga cgt cga ggc agg tca cct aga aga aga act       481
Glu Thr Thr Val Val Arg Arg Arg Gly Arg Ser Pro Arg Arg Arg Thr
145                 150                 155                 160 cct tcg cct cgc agg cga agg tct caa tcg ccg cgg cga aga tct       529
Pro Ser Pro Arg Arg Arg Arg Ser Gln Ser Pro Arg Arg Arg Ser
                165                 170                 175 caa tct cgg gaa tct caa tgt tag tga                                    556
Gln Ser Arg Glu Ser Gln Cys
```

-continued

180

<210> SEQ ID NO 4
<211> LENGTH: 183
<212> TYPE: PRT
<213> ORGANISM: Hepatitis B virus

<400> SEQUENCE: 4

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 5
<211> LENGTH: 185
<212> TYPE: PRT
<213> ORGANISM: Hepatitis B virus

<400> SEQUENCE: 5

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro

```
                130                 135                 140
Glu Thr Thr Val Val Arg Arg Arg Asp Arg Gly Arg Ser Pro Arg Arg
145                 150                 155                 160

Arg Thr Pro Ser Pro Arg Arg Arg Ser Gln Ser Pro Arg Arg
                165                 170                 175

Arg Ser Gln Ser Arg Glu Ser Gln Cys
            180                 185

<210> SEQ ID NO 6
<211> LENGTH: 22
<212> TYPE: DNA
<213> ORGANISM: Artificial Sequence
<220> FEATURE:
<223> OTHER INFORMATION: Synthetic CpG-B 1018

<400> SEQUENCE: 6
tgactgtgaa cgttcgagat ga                                          22

<210> SEQ ID NO 7
<211> LENGTH: 20
<212> TYPE: DNA
<213> ORGANISM: Artificial Sequence
<220> FEATURE:
<223> OTHER INFORMATION: Synthetic CpG-A  D19

<400> SEQUENCE: 7
ggtgcatcga tgcagggggg                                             20

<210> SEQ ID NO 8
<211> LENGTH: 21
<212> TYPE: DNA
<213> ORGANISM: Artificial Sequence
<220> FEATURE:
<223> OTHER INFORMATION: Synthetic CpG-C C274

<400> SEQUENCE: 8
tcgtcgaacg ttcgagatga t                                           21

<210> SEQ ID NO 9
<211> LENGTH: 25
<212> TYPE: DNA
<213> ORGANISM: Artificial Sequence
<220> FEATURE:
<223> OTHER INFORMATION: Synthetic CpG-C C695

<400> SEQUENCE: 9
tcgaacgttc gaacgttcga acgtt                                       25

<210> SEQ ID NO 10
<211> LENGTH: 88
<212> TYPE: DNA
<213> ORGANISM: Artificial Sequence
<220> FEATURE:
<223> OTHER INFORMATION: Synthetic ISS

<400> SEQUENCE: 10
ggtgcatcga tgcagggggg tgactgtgaa cgttcgagat gatcgtcgaa cgttcgagat 60
gattcgaacg ttcgaacgtt cgaacgtt                                    88

<210> SEQ ID NO 11
<211> LENGTH: 35
<212> TYPE: DNA
<213> ORGANISM: Artificial Sequence
<220> FEATURE:
```

<223> OTHER INFORMATION: Synthetic primer HBc-1

<400> SEQUENCE: 11
gccatggata tcgatcctta taaagaattc ggagc                                35

<210> SEQ ID NO 12
<211> LENGTH: 54
<212> TYPE: DNA
<213> ORGANISM: Artificial Sequence
<220> FEATURE:
<223> OTHER INFORMATION: Synthetic primer Lp(a)-1

<400> SEQUENCE: 12
gttaacttgg aagatccagc tatcactgag gctccttccg aacaagcacc gact          54

<210> SEQ ID NO 13
<211> LENGTH: 36
<212> TYPE: DNA
<213> ORGANISM: Artificial Sequence
<220> FEATURE:
<223> OTHER INFORMATION: Synthetic primer HBc-2

<400> SEQUENCE: 13
ggcctctcac taacattgag attcccgaga ttgaga                              36

<210> SEQ ID NO 14
<211> LENGTH: 55
<212> TYPE: DNA
<213> ORGANISM: Artificial Sequence
<220> FEATURE:
<223> OTHER INFORMATION: Synthetic primer Lp(a)-2

<400> SEQUENCE: 14
ttccgaacaa gcaccgactg agcaaagggg tgctactagc agggacctgg tagtc         55

<210> SEQ ID NO 15
<211> LENGTH: 609
<212> TYPE: DNA
<213> ORGANISM: Artificial Sequence
<220> FEATURE:
<223> OTHER INFORMATION: Synthetic HBc-apo(a) chimera
<220> FEATURE:
<221> NAME/KEY: CDS
<222> LOCATION: (4)..(606)

<400> SEQUENCE: 15

```
gcc atg gat atc gat cct tat aaa gaa ttc gga gct act gtg gag tta    48
    Met Asp Ile Asp Pro Tyr Lys Glu Phe Gly Ala Thr Val Glu Leu
    1               5                  10                  15 ctc tcg ttt ctc ccg agt gac ttc ttt cct tca gta cga gat ctt ctg    96
Leu Ser Phe Leu Pro Ser Asp Phe Phe Pro Ser Val Arg Asp Leu Leu
                20                  25                  30 gat acc gcc agc gcg ctg tat cgg gaa gcc ttg gag tct cct gag cac   144
Asp Thr Ala Ser Ala Leu Tyr Arg Glu Ala Leu Glu Ser Pro Glu His
            35                  40                  45 tgc agc cct cac cat act gcc ctc agg caa gca att ctt tgc tgg ggg   192
Cys Ser Pro His His Thr Ala Leu Arg Gln Ala Ile Leu Cys Trp Gly
        50                  55                  60 gag ctc atg act ctg gcc acg tgg gtg ggt gtt aac ttg gaa gat cca   240
Glu Leu Met Thr Leu Ala Thr Trp Val Gly Val Asn Leu Glu Asp Pro
    65                  70                  75 gct atc act gag gct cct tcc gaa caa gca ccg act gag caa agg ggt   288
Ala Ile Thr Glu Ala Pro Ser Glu Gln Ala Pro Thr Glu Gln Arg Gly
80                  85                  90                  95
```

```
gct act agc agg gac ctg gta gtc agt tat gtc aac act aat atg ggt      336
Ala Thr Ser Arg Asp Leu Val Val Ser Tyr Val Asn Thr Asn Met Gly
            100                 105                 110 tta aag ttc agg caa ctc ttg tgg ttt cac att agc tgc ctc act ttc      384
Leu Lys Phe Arg Gln Leu Leu Trp Phe His Ile Ser Cys Leu Thr Phe
            115                 120                 125 ggc cga gaa aca gtt cta gaa tat ttg gtg tct ttc gga gtg tgg atc      432
Gly Arg Glu Thr Val Leu Glu Tyr Leu Val Ser Phe Gly Val Trp Ile
            130                 135                 140 cgc act cct cca gct tat agg cct ccg aat gcc cct atc ctg tcg aca      480
Arg Thr Pro Pro Ala Tyr Arg Pro Pro Asn Ala Pro Ile Leu Ser Thr
145                 150                 155                 160 ctc ccg gag act act gtt gtt aga cgt cga ggc agg tca cct aga aga      528
Leu Pro Glu Thr Thr Val Val Arg Arg Arg Gly Arg Ser Pro Arg Arg
            165                 170                 175 aga act cct tcg cct cgc agg cga agg tct caa tcg ccg cgg cgc cga      576
Arg Thr Pro Ser Pro Arg Arg Arg Ser Gln Ser Pro Arg Arg Arg
            180                 185                 190 aga tct caa tct cgg gaa tct caa tgt tag tga                          609
Arg Ser Gln Ser Arg Glu Ser Gln Cys
            195                 200
```

<210> SEQ ID NO 16
<211> LENGTH: 200
<212> TYPE: PRT
<213> ORGANISM: Artificial Sequence
<220> FEATURE:
<223> OTHER INFORMATION: Synthetic Construct

<400> SEQUENCE: 16

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Val Asn Leu Glu Asp Pro Ala
65                  70                  75                  80

Ile Thr Glu Ala Pro Ser Glu Gln Ala Pro Thr Glu Gln Arg Gly Ala
                85                  90                  95

Thr Ser Arg Asp Leu Val Val Ser Tyr Val Asn Thr Asn Met Gly Leu
            100                 105                 110

Lys Phe Arg Gln Leu Leu Trp Phe His Ile Ser Cys Leu Thr Phe Gly
        115                 120                 125

Arg Glu Thr Val Leu Glu Tyr Leu Val Ser Phe Gly Val Trp Ile Arg
    130                 135                 140

Thr Pro Pro Ala Tyr Arg Pro Pro Asn Ala Pro Ile Leu Ser Thr Leu
145                 150                 155                 160

Pro Glu Thr Thr Val Val Arg Arg Arg Gly Arg Ser Pro Arg Arg Arg
                165                 170                 175

Thr Pro Ser Pro Arg Arg Arg Ser Gln Ser Pro Arg Arg Arg
            180                 185                 190

Ser Gln Ser Arg Glu Ser Gln Cys
        195                 200
```

<210> SEQ ID NO 17

```
<211> LENGTH: 16
<212> TYPE: PRT
<213> ORGANISM: Homo sapiens

<400> SEQUENCE: 17

Met Glu His Lys Glu Val Val Leu Leu Leu Leu Phe Leu Lys Ser
1               5                   10                  15
```

DNA VACCINE CONTAINING SPECIFIC EPITOPE OF APOLIPOPROTEIN (A)

CROSS-REFERENCE TO THE RELATED APPLICATIONS

The present application is a divisional of U.S. patent application Ser. No. 14/032,804, filed on Sep. 20, 2013, which claims the benefit of Japanese Patent Application No. 2012-208796, filed Sep. 21, 2012, the contents of which are incorporated in full herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 31,311 bytes ASCII (Text) file named "725867SequenceListing.txt," created Jun. 30, 2016.

TECHNICAL FIELD OF THE INVENTION

The present invention relates to a DNA vaccine effective for the treatment or prophylaxis of a lipoprotein(a)-related diseases such as arteriosclerosis.

BACKGROUND OF THE INVENTION

Lipoprotein(a) [Lp(a)] is a serum lipoprotein consisting of one molecule of apolipoprotein B-100 (apoB) and one molecule of apolipoprotein(a) [apo(a)], which are bonded through a single disulfide bond; and a cholesterol-rich low-density lipoprotein (LDL) particle, (non-patent document 1), and found only in humans, primates and hedgehog. The apo(a) is a homologue of plasminogen (non-patent document 2), containing 10 different types (kringle-4 types 1 through 10) of plasminogen kringle-4 like repeats as well as regions homologous to the kringle-5 and inactive protease regions (non-patent document 3). Lp(a) has been considered as an independent cardiovascular risk factor and several studies have shown the association between plasma Lp(a) levels and cardiovascular disease (CVD)/coronary heart disease (CHD). Elevated Lp(a) levels promote atherosclerosis via Lp(a)-derived cholesterol entrapment in intima; via inflammatory cell recruitment; and/or via the binding of pro-inflammatory-oxidized phospholipids (non-patent document 4). Lipid lowering agents have little effect on plasma Lp(a) level (non-patent document 5). Although it has been reported that administration of niacin or estrogen may reduce the Lp(a) levels, there is no specific agent for the reduction of plasma Lp(a) (non-patent document 6-8).

Non-patent document 9 discloses a measurement method of Lp(a) which is not influenced by the polymorphism of apo(a).

While vaccine is often used for the prophylaxis or treatment of diseases caused by exogenous factors, such as infections and the like, even for the diseases caused by endogenous aggravation factors such as Alzheimer's disease, hypertension and the like, vaccine therapy has been tried, which includes administering the aggravation factors, epitopes contained in the aggravation factors, or expression vectors encoding them to patients to induce the antibody to the aggravation factor in the body of patients, thereby neutralizing the function of the aggravation factor and mitigating the symptoms of the target disease (non-patent documents 10-12). Plasmid DNA vaccination is one of the tools to induce both humoral and cellular immune responses, without co-treatment with adjuvant, because in the case of plasmid DNA, unmethylated CpG motifs expressed with a plasmid unmethylated CpG motifs expressed with a plasmid backbone have been considered to be "built-in" adjuvants, owing to their ability to activate the innate immune system by means of TLR9 (non-patent document 13). In addition, recent accumulating evidence suggests that the double-stranded structure of DNA, independently of CpG motifs, possesses immunomodulatory effects when introduced into the cytosol or its homeostatic clearance is hampered.

However, when the aggravation factor is endogenous, the immune tolerance to the factor has generally been established since the factor is the patient's own component. Therefore, it is difficult to efficiently induce an antibody to the factor in the body of the patient even when these endogenous aggravation factors or partial peptides thereof are directly administered to the patient. As such, some technical idea is necessary to have the patient's immune system recognize these self antigens, thereby inducing the production of the antibody.

Hepatitis B virus core (HBc) antigen protein constitutes spherical core particles by self assembly. The core particles have very high immunogenicity. When a fusion polypeptide obtained by inserting a desired epitope into a particular site of the HBc antigen protein, or connecting a desired epitope to the terminus of the HBc antigen protein is used, the epitope is presented on the surface of the particles formed by self-assembly. Using the fusion polypeptide, the inserted epitope is easily recognized by the immune system, and the production of the antibody that recognizes the epitope can be efficiently induced. Therefore, utilizing the HBc antigen protein as a platform of vaccine, attempts have been made to induce production of the antibody to an antigen difficult to be recognized by the immune system (non-patent document 14, non-patent document 15).

Patent document 1 discloses particles composed of a chimeric HBc antigen protein containing an foreign amino acid sequence having an epitope, wherein the foreign amino acid sequence is inserted into the amino acid residues 80-81 of the HBc antigen.

Non-patent document 16 describes that intramuscular immunization with a DNA vaccine encoding ISS and an HBc antigen inserted with a CETP epitope consisting of 26 amino acids inhibited atherosclerosis in rabbit atherosclerosis model.

However, even if production of an antibody to an endogenous aggravation factor can be induced, when cellular immunity to the factor is simultaneously induced, side effects are caused by the autoimmune reaction. Therefore, it is necessary to efficiently induce the production of an antibody to the endogenous aggravation factor while suppressing the induction of self-reactive T cells.

Under the above situation, a DNA vaccine showing totally satisfying effectiveness to arteriosclerosis has not been developed yet.

DOCUMENT LIST

Patent Document patent document 1: JP-B-3228737

Non-Patent Documents non-patent document 1: Acta Pathologica Microbiologica Scandinavica, 1963, 59: 369-382 non-patent document 2: Proceedings of the National Academy of Sciences, 1987, 84: 3224
non-patent document 3: Nature, 1987, 330: 132-137
non-patent document 4: Nature, 1989 May 25; 339(6222): 301-303
non-patent document 5: Journal of Clinical Investigation, 1990, 85: 1709
non-patent document 6: New England journal of medicine, 1990, 323: 1289-1298
non-patent document 7: New England journal of medicine, 2009, 361: 2113-2122
non-patent document 8: Atherosclerosis, 2010, 211: 41-47
non-patent document 9: Clinica chimica acta, 1999, 287: 29-43
non-patent document 10: Nature, 2000, 408: 982-985
non-patent document 11: Nat Rev Neurosci, 2002, 3: 824-828
non-patent document 12: The Lancet, 2008, 371: 821-827
non-patent document 13: Nature, 2008, 451: 725-729
non-patent document 14: Expert Rev. Vaccines, vol. 8, no. 11, pp. 1565-1573, 2009
non-patent document 15: Nature, vol. 330, pp. 381-384, 1987
non-patent document 16: Vaccine, 2006, 24: 4942-4950

SUMMARY OF THE INVENTION

The present invention aims to provide a DNA vaccine capable of treating or preventing a lipoprotein(a)-related diseases such as arteriosclerosis while avoiding the induction of self-reactive T cells.

The present inventors have conducted intensive studies and found that administration of an expression vector for chimeric Hepatitis B virus core antigen polypeptide obtained by inserting a specific epitope of apolipoprotein (a) between the amino acid residues 80 and 81 of hepatitis B virus core antigen polypeptide dominantly induces humoral immunity to apolipoprotein (a) while suppressing the induction of T cells that react with apolipoprotein (a), whereby deposition of lipoprotein (a) and vascular intimal thickening can be effectively suppressed. Based on these findings, they have further studied and completed the present invention.

Accordingly, the present invention relates to the following.

[1] A method for treating or preventing a lipoprotein(a)-related disease in a mammal, comprising administering effective amount of an expression vector encoding an antigen polypeptide inserted with an amino acid sequence comprising a specific epitope of apolipoprotein (a) in the mammal.

[2] The method of [1], wherein a neutralizing antibody against lipoprotein(a) is produced by administering the expression vector.

[3] The method of [2], wherein the neutralizing antibody suppresses deposition of lipoprotein(a) to a vascular tissue.

[4] The method of [2], wherein the neutralizing antibody decreases the amount of an inflammatory cytokine in a blood.

[5] The method of [3], wherein the lipoprotein(a)-related disease is arteriosclerosis.

[6] The method of [4], wherein the lipoprotein(a)-related disease is arteriosclerosis.

[7] The method of [1], wherein the antigen polypeptide is a chimeric Hepatitis B virus core antigen polypeptide inserted with an amino acid sequence comprising a specific epitope of apolipoprotein (a), wherein the amino acid sequence comprising the specific epitope is inserted between the amino acid residues 80 and 81 of the hepatitis B virus core antigen polypeptide.

[8] The method of [7], wherein the lipoprotein(a)-related disease is arteriosclerosis.

[9] The method of [8], wherein the arteriosclerosis is atherosclerosis.

[10] The method of [7], wherein the inserted amino acid sequence comprises the amino acid shown by SEQ ID NO: 1.

[11] The method of [10], wherein the inserted amino acid sequence further comprises one or more specific epitopes.

[12] The method of [11], wherein the further specific epitope is a specific epitope of apolipoprotein B.

[13] The method of [1], wherein the expression vector is administered plural times.

[14] The method of [13], wherein the expression vector is administered 2, 3 or 4 times.

[15] A method of inducing a neutralizing antibody against lipoprotein(a) in a mammal, comprising administering effective amount of an expression vector encoding an antigen polypeptide inserted with an amino acid sequence comprising a specific epitope of apolipoprotein (a) in the mammal.

[16] An expression vector encoding a chimeric Hepatitis B virus core antigen polypeptide inserted with an amino acid sequence comprising a specific epitope of apolipoprotein (a), wherein the amino acid sequence comprising the specific epitope is inserted between the amino acid residues 80 and 81 of the hepatitis B virus core antigen polypeptide.

[17] The expression vector of [16], wherein the inserted amino acid sequence comprises the amino acid shown by SEQ ID NO: 1.

[18] The expression vector of [16], wherein the inserted amino acid sequence further comprises one or more specific epitopes.

[I] An agent for the treatment or prophylaxis of arteriosclerosis comprising an expression vector encoding a chimeric Hepatitis B virus core antigen polypeptide inserted with an amino acid sequence comprising a specific epitope of apolipoprotein (a), wherein the amino acid sequence comprising the specific epitope is inserted between the amino acid residues 80 and 81 of the hepatitis B virus core antigen polypeptide.

[II] The agent of [I], wherein the arteriosclerosis is atherosclerosis.

[III] The agent of [I] or [II], wherein the inserted amino acid sequence comprises the amino acid sequence represented by SEQ ID NO: 1.

[IV] The agent of any of [I]-[III], wherein the inserted amino acid sequence further comprises one or more specific epitopes.

[V] The agent of [IV], wherein the further specific epitope is a specific epitope of apolipoprotein B.

[VI] The agent of any of [I]-[V], which is administered plural times.

[VII] The agent of [VI], which is administered 2, 3 or 4 times.

[VIII] An expression vector encoding a chimeric Hepatitis B virus core antigen polypeptide inserted with an amino acid sequence comprising a specific epitope of apolipoprotein (a), for use in the treatment or prophylaxis of arteriosclerosis, wherein the amino acid sequence comprising the specific epitope is inserted between the amino acid residues 80 and 81 of the hepatitis B virus core antigen polypeptide.

[IX] The expression vector of [VIII], wherein the arteriosclerosis is atherosclerosis.
[X] The expression vector of [VIII] or [IX], wherein the inserted amino acid sequence comprises the amino acid shown by SEQ ID NO: 1.
[XI] The expression vector of any of [VIII]-[X], wherein the inserted amino acid sequence further comprises one or more specific epitopes.

Effect of the Invention

The present invention provides a DNA vaccine capable of treating or preventing arteriosclerosis while avoiding induction of self-reactive T cells.

Since the vaccine of the present invention dominantly induces humoral immunity to apolipoprotein (a) rather than the cellular immunity, the risk of an adverse influence of the self-reactive cellular immunity can be reduced.

DESCRIPTION OF EMBODIMENTS

Figure 1:
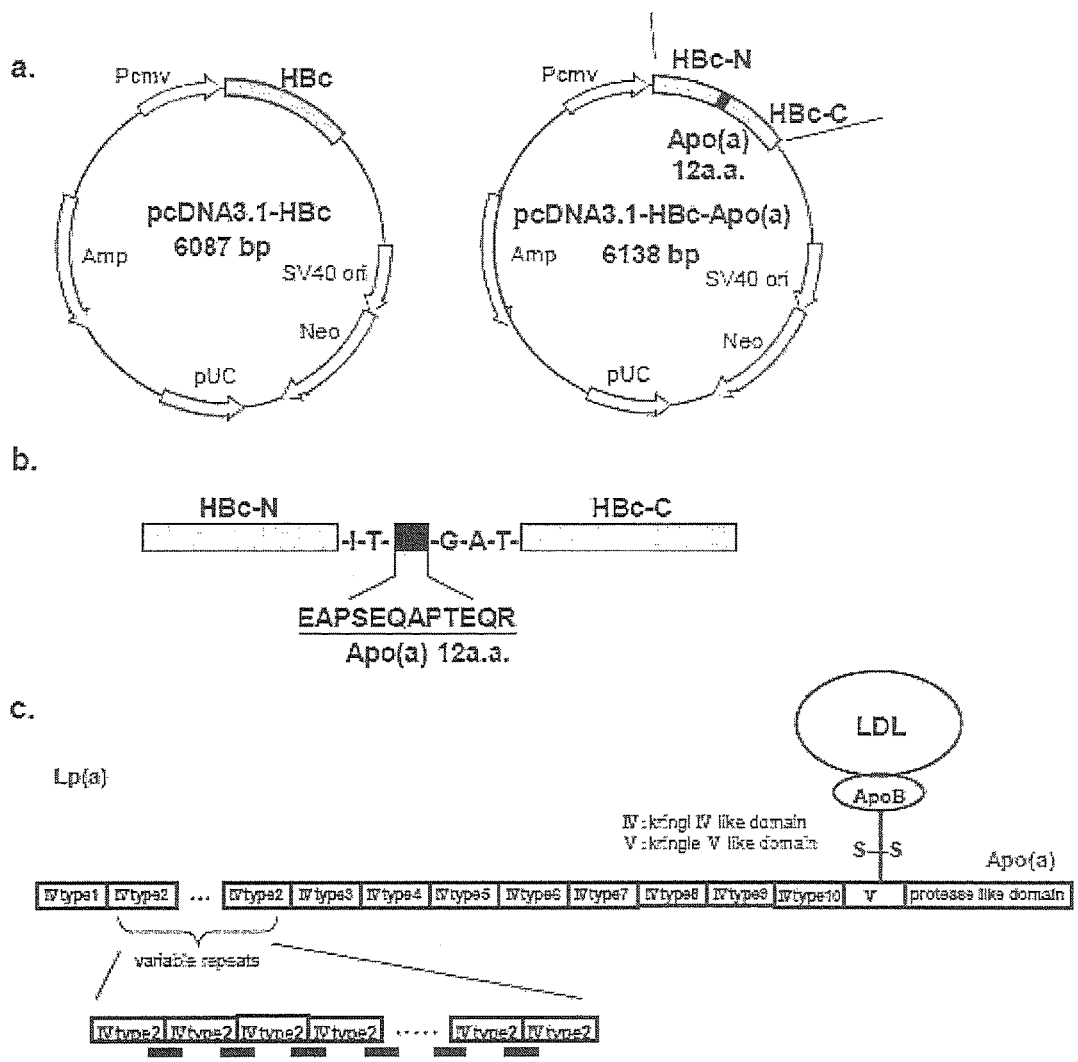
FIG. 1 shows plasmid DNA construction for vaccination. a) Plasmid map of pcDNA3.1-HBc (control vector) and pcDNA3.1-HBc-apo(a) (vaccination vector). HBc indicates the full sequence of HBc. HBc-N indicates the N-terminus of HBc (1-80 a.a.) and HBc-C indicates the C-terminus of HBc (81-183 a.a.). b) The detail information of plasmid design for Apo(a) vaccine. Twelve amino acids (EAPSEQAPTEQR: SEQ ID NO: 1) as an antigen for Apo(a) and linkers (the N-terminal I-T dipeptide linker and the C-terminal G-A-T tripeptide) were designed to inframe fusion to HBc to allow flexibility in the conformation of apo(a) epitope when surface-exposed on HBc particle. The apo(a) and the linkers were represented by single-letter codes. c) Schema of Lp(a) showing the targeted antigen. Apo(a) is mainly composed of kringle IV like domain (1-10) and kringle V like domain, and repeated kringle IV domain type2 (IV type2) is variable repeats. Black box indicates the epitope (EAPSEQAPTEQR: SEQ ID NO: 1) which is overlapped in repeated sequences of kringle-4 type 2 of apo(a) and multiply presented in the repeated kringle IV domain type2 domain.

The present invention provides an agent for the treatment or prophylaxis of a lipoprotein(a)-related disease, comprising an expression vector encoding an antigen polypeptide inserted with an amino acid sequence comprising a specific epitope of apolipoprotein (a). By administering effective amount of the expression vector encoding an antigen polypeptide inserted with an amino acid sequence comprising a specific epitope of apolipoprotein (a) in a mammal, a lipoprotein(a)-related disease in the mammal can be treated or prevented.

Though not bound by theory, by administering an effective amount of the expression vector encoding an antigen polypeptide inserted with an amino acid sequence comprising a specific epitope of apolipoprotein (a) in a mammal, production of an antibody against apolipoprotein (a) is induced in the mammal, and the induced antibody acts as a neutralizing antibody against lipoprotein (a), suppresses deposition of lipoprotein (a) to the vascular tissue, or inhibits production of inflammatory cytokines (e.g. IL-1β, TNF-α, MCP-1) in macrophages and the like induced by lipoprotein (a) stimulation to decrease the amount of inflammatory cytokines in blood, thereby treating or preventing lipoprotein(a)-related diseases. The present invention also provides a method of inducing a neutralizing antibody against lipoprotein(a) in a mammal, comprising administering effective amount of an expression vector encoding an antigen polypeptide inserted with an amino acid sequence comprising a specific epitope of apolipoprotein (a) in the mammal.

In one embodiment, the expression vector encoding an antigen polypeptide comprising a specific epitope of apolipoprotein (a) is an expression vector encoding a chimeric Hepatitis B virus core antigen polypeptide inserted with an amino acid sequence comprising a specific epitope of apolipoprotein (a), wherein the amino acid sequence comprising the specific epitope is inserted between the amino acid residues 80 and 81 of the hepatitis B virus core antigen polypeptide.

When an expression vector encoding a chimeric Hepatitis B virus core antigen polypeptide inserted with an amino acid sequence comprising a specific epitope of apolipoprotein (a) is administered, an immune reaction (preferably humoral immune reaction such as antibody production and the like) to the specific epitope of apolipoprotein (a) in the expressed chimeric Hepatitis B virus core antigen polypeptide is induced, and production of lipoprotein (a) is suppressed by an antibody to apolipoprotein (a), whereby neointimal formation and vascular intimal thickening are suppressed.

Lipoprotein(a)-related disease refers to a disease caused by decreased function of endothelial cells, abnormal proliferation of vascular smooth muscle cells, or inflammatory cytokines produced by macrophages and the like, induced by lipoprotein (a) stimulation due to deposition of lipoprotein (a) to inner wall of blood vessel. Examples of the lipoprotein(a)-related disease include cerebral infarction, myocardial infarction, angina, sclerosis obliterans, vascular dementia, vascular restenosis and the like caused by arteriosclerosis. Preferable lipoprotein(a)-related disease is arteriosclerosis. While the kind of arteriosclerosis to be the target of the therapeutic or prophylactic agent of the present invention is not limited, it is preferably atherosclerosis.

In the present invention, use of apolipoprotein (a) derived from a mammal to be the application target of the therapeutic or prophylactic agent of the present invention is intended though without limitation thereto. The application target of the therapeutic or prophylactic agent of the present invention is a mammal expressing apolipoprotein (a). As a mammal expressing apolipoprotein (a), only primates such as human and the like and hedgehog are known. The application target of the therapeutic or prophylactic agent of the present invention is preferably a primate such as human. Therefore, for example, when the therapeutic or prophylactic agent of the present invention is applied to human, use of apolipoprotein (a) derived from human is intended though without limitation thereto.

In the present specification, regarding the particular factor X (polypeptide or polynucleotide), "factor X derived from organism Y" or "organism Y factor X" means that the amino acid sequence or nucleic acid sequence of factor X has the same or substantially the same amino acid sequence or nucleic acid sequence as the amino acid sequence or nucleic acid sequence of factor X naturally expressed in organism Y. Being "substantially the same" means that the amino acid sequence or nucleic acid sequence of interest has not less than 70% (preferably not less than 80%, more preferably not less than 90%, still more preferably not less than 95%, most preferably not less than 99%) identity with the amino acid sequence or nucleic acid sequence of factor X naturally expressed in organism Y, and the function of factor X is maintained.

Apolipoprotein (a) is a known angiogenesis factor, and the amino acid sequence and cDNA sequence thereof are also known. It is known that apolipoprotein (a) contains kringle-IV type 2 repeat sequences and the repeat number thereof varies. Those having repeat sequences with any repeat number are encompassed in apolipoprotein (a). The representative amino acid sequence of human apolipoprotein (a) includes, but is not limited to, the amino acid sequence shown by SEQ ID NO: 2(NP_005568.2). As a partial amino acid sequence of human apolipoprotein (a), SEQ ID NO: 17 (AAB49909, AAB66587) has been reported.

In the present specification, "epitope" refers to a basic element or minimum unit for recognition by each antibody or T cell receptor, which is a particular domain, region or molecular structure the aforementioned antibody or T cell receptor binds to.

The epitope of apolipoprotein (a) used in the present invention is specific to the apolipoprotein (a). Being "specific" means that a gene product (excluding variable regions of immunoglobulin and T cell receptor) other than apolipoprotein (a) naturally expressed in a mammal from which the apolipoprotein (a) is derived does not include said epitope.

As a specific epitope of apolipoprotein (a) used in the present invention, preferably selected is one at a position inhibiting the deposition of lipoprotein (a) to the vascular intima when an antibody recognizing the epitope binds to the epitope. Such epitope may be present in, for example, the kringle-IV type 2 repeat sequences. An epitope contained in the region removed during the maturation process of apolipoprotein (a) such as signal sequence and the like is preferably eliminated from the epitope used in the present invention.

The length of the amino acid sequence of the epitope is generally 5-30 amino acids, preferably 6-25 amino acids, more preferably 10-18 amino acids, further more preferably 11-16 amino acids. When the amino acid sequence is too short, the antigenicity of the epitope may be lost. When the amino acid sequence is too long, chimeric hepatitis B virus core antigen polypeptide does not easily form core particles due to self-assembly, as a result of which an antibody that specifically recognizes the epitope may not be produced, and a superior treatment or improvement effect on lipoprotein (a)-related diseases including arteriosclerosis may not be obtained.

Specific examples of preferable epitope of apolipoprotein (a) include the following.

EAPSEQAPTEQR (SEQ ID NO: 1)

SEQ ID NO: 1 is a partial amino acid sequence of human apolipoprotein (a).

Hepatitis B virus core antigen polypeptide used in the present invention is (1) a polypeptide containing the amino acid sequence shown by SEQ ID NO: 4, or (2) a polypeptide containing an amino acid sequence having not less than 90% (preferably not less than 95%, more preferably not less than 97%, still more preferably not less than 99%) identity with the amino acid sequence shown by SEQ ID NO: 4, and having an activity to form core particles due to self-assembly.

Self-assembly refers to a phenomenon wherein molecules dissolved in a solution associate to form an assembly. Core particle refers to a rigid structure having a specific repetitive constitution. In the present specification, the core particle may be a product of synthesis steps or a product of biological steps.

As the polypeptide of the embodiment of (2), a polypeptide containing the amino acid sequence shown by SEQ ID NO: 5 disclosed in WO2003/031466 can be mentioned. A polypeptide containing the amino acid sequence shown by SEQ ID NO: 5 except that one or plural cysteine residues of the positions 48, 61, 107 and 185 are deleted or substituted by other amino acid residue (e.g., serine residue) is also preferable as the polypeptide of the embodiment of (2). As recognized by those of ordinary skill in the art, in a polypeptide having an amino acid sequence different from that of SEQ ID NO: 5, cysteine residues at similar positions can be deleted or substituted by other amino acid residues, and polypeptides obtained by such deletion and substitution are also encompassed in the polypeptide of the embodiment of (2).

The polypeptide of the embodiment of (2) also encompasses a variant polypeptide wherein the isoleucine residue at the position corresponding to the position 97 of SEQ ID NO: 5 is substituted by leucine residue or phenylalanine residue (Yuan et al., J. Virol. vol. 73, pages 10122-10128 (1999)). In addition, amino acid sequences of many HBcAg variants and several kinds of hepatitis B core antigen precursor variants are disclosed in GenBank reports AAF121240, AF121239, X85297, X02496, X85305, X85303, AF151735, X85259, X85286, X85260, X85317, X85298, AF043593, M20706, X85295, X80925, X85284, X85275, X72702, X85291, X65258, X85302, M32138, X85293, X85315, U95551, X85256, X85316, X85296, AB033559, X59795, X8529, X85307, X65257, X85311, X85301, X85314, X85287, X85272, X85319, AB010289, X85285, AB010289, AF121242, M90520, P03153, AF110999 and M95589 (each of the disclosures is incorporated in the present specification by reference), and polypeptides containing amino acid sequences of these variants are also encompassed in the polypeptide of the embodiment of (2). The above-mentioned variants have amino acid sequences different at many positions including amino acid residues corresponding to the amino acid residues present at the positions 12, 13, 21, 22, 24, 29, 32, 33, 35, 38, 40, 42, 44, 45, 49, 51, 57, 58, 59, 64, 66, 67, 69, 74, 77, 80, 81, 87, 92, 93, 97, 98, 100, 103, 105, 106, 109, 113, 116, 121, 126, 130, 133, 135, 141, 147, 149, 157, 176, 178, 182 and 183 in SEQ ID NO: 5.

Furthermore, polypeptides containing the amino acid sequences of the HBcAg variants described in WO01/98333, WO01/77158 and WO02/14478, all of which are incorporated in the present specification by reference are also encompassed in the polypeptide of the embodiment of (2).

In the present specification, unless particularly indicated, the positions of amino acid residues in the amino acid sequence of hepatitis B virus core antigen polypeptide are specified with the amino acid sequence shown by SEQ ID NO: 4 as the standard. When a polypeptide does not contain the amino acid sequence shown by SEQ ID NO: 4, the amino acid sequence of the polypeptide is aligned with the amino acid sequence shown by SEQ ID NO: 4, and the position of the corresponding amino acid residue is adopted.

The hepatitis B virus core antigen polypeptide used in the present invention is preferably a polypeptide containing the amino acid sequence shown by SEQ ID NO: 4.

In the chimeric hepatitis B virus core antigen polypeptide to be used in the present invention, an amino acid sequence comprising a specific epitope of apolipoprotein (a) is inserted between the amino acid residues 80 and 81 of the hepatitis B virus core antigen polypeptide. That is, the chimeric hepatitis B virus core antigen polypeptide to be used in the present invention contains the following elements (a)-(c):

(a) N-terminus part polypeptide residues of hepatitis B virus core antigen polypeptide (consisting of the continuous partial amino acid sequence of hepatitis B virus core antigen polypeptide from N-terminus to the amino acid residue 80),
(b) an amino acid sequence consisting of a specific epitope of apolipoprotein (a), and
(c) C-terminal partial polypeptide residues of hepatitis B virus core antigen polypeptide (consisting of the continuous partial amino acid sequence of hepatitis B virus core antigen polypeptide from the amino acid residue 81 to C-terminus) in the order of (a), (b), (c) from the N terminal side.

The chimeric hepatitis B virus core antigen polypeptide to be used in the present invention having the above-mentioned constitution forms core particles due to self-assembly, and a specific epitope of apolipoprotein (a) is presented on the outside of the particles.

The inserted amino acid sequence between element (a) and element (c) may further contain, in addition to element (b) (amino acid sequence consisting of specific epitopes of apolipoprotein (a)), one or more (preferably 1-3, more preferably 1) specific epitope. As the further specific epitope, a specific epitope, which is an aggravation factor of arteriosclerosis other than apolipoprotein (a), is used. Examples of the further specific epitope include, but are not limited to, apolipoprotein B and the like. The further specific epitope may be inserted at any position between element (a) and element (b), and between element (b) and element (c). The length of the amino acid sequence of the further specific epitope is generally 5-30 amino acids, preferably 6-25 amino acids, more preferably 10-18 amino acids, further more preferably 11-16 amino acids.

When plural specific epitopes are inserted between constituent element (a) and constituent element (c), the specific epitopes may be directly connected by a covalent bond or via a spacer sequence. The spacer sequence means an amino acid sequence containing one or more amino acid residues, which is inserted between two adjacent elements contained in chimeric hepatitis B virus core antigen polypeptide. Specific epitopes are preferably connected via a spacer sequence so that plural specific epitopes will be stably presented while maintaining their structures. While the length of the spacer sequence is not limited as long as the chimeric hepatitis B virus core antigen polypeptide forms core particles due to self-assembly and all inserted specific epitopes are presented on the outside of the particles, it is generally 1-10 amino acids, preferably 1-5 amino acids, more preferably 1-3 amino acids, most preferably 2 or 3 amino acids.

A specific epitope between element (a) and element (c), which is the closest to the N terminus, and element (a) may be directly connected by a covalent bond or via a spacer sequence. The element (a) and the specific epitope between element (a) and element (c), which is the closest to the N terminus, are preferably connected via a spacer sequence so that a specific epitope of apolipoprotein (a) will be stably presented on the outside of the particles formed by self-assembly of chimeric hepatitis B virus core antigen polypeptides, while maintaining its structure. While the length of the spacer sequence is not limited as long as chimeric hepatitis B virus core antigen polypeptide forms core particles due to self-assembly and a specific epitope of apolipoprotein (a) is presented on the outside of the particles, it is generally 1-10 amino acids, preferably 1-5 amino acids, more preferably 1-3 amino acids, most preferably 2 or 3 amino acids. Also, the kind of the spacer sequence is not limited as long as chimeric hepatitis B virus core antigen polypeptide forms core particles due to self-assembly and a specific epitope of apolipoprotein (a) is presented on the outside of the particles. Examples of a preferable spacer sequence include, but are not limited to, IT, GAT, CGG and the like.

A specific epitope between element (a) and element (c), which is the closest to the C terminus, and element (c) may be directly connected by a covalent bond or via a spacer sequence. The element (b) and element (c) are preferably connected via a spacer sequence so that a specific epitope of apolipoprotein (a) will be stably presented on the outside of the particles formed by self-assembly of chimeric hepatitis B virus core antigen polypeptides, while maintaining its structure. While the length of the spacer sequence is not limited as long as chimeric hepatitis B virus core antigen polypeptide forms core particles due to self-assembly and an epitope of apolipoprotein (a) is presented on the outside of the particles, it is generally 1-amino acids, preferably 1-5 amino acids, more preferably 1-3 amino acids, most preferably 2 or 3 amino acids. Also, the kind of the spacer sequence is not limited as long as chimeric hepatitis B virus core antigen polypeptide forms core particles due to self-assembly and a specific epitope of apolipoprotein (a) is presented on the outside of the particles. Examples of a preferable spacer sequence include, but are not limited to, IT, GAT, CGG and the like.

While the length of the inserted amino acid sequence between element (a) and element (c) is not limited as long as chimeric hepatitis B virus core antigen polypeptide forms core particles due to self-assembly, a specific epitope of apolipoprotein (a) is presented on the outside of the particles, and arteriosclerosis can be treated or prevented, it is generally 5-80 amino acids. When the inserted amino acid sequence is too short, the antigenicity of the epitope may be lost. When the inserted amino acid sequence is too long, chimeric hepatitis B virus core antigen polypeptide does not easily form core particles due to self-assembly, as a result of which an antibody that specifically recognizes the inserted epitope is not produced, and a good treatment or improvement effect on lipoprotein (a)-related diseases including arteriosclerosis may not be achieved.

The expression vector used in the present invention is a recombinant vector incorporating a polynucleotide encoding the above-mentioned chimeric hepatitis B virus core antigen polypeptide. When the expression vector is administered to a target mammal, the expression vector is intracellularly incorporated into the target mammal, and the cell expresses the above-mentioned chimeric hepatitis B virus core antigen polypeptide. Examples of the expression vector inserted with polynucleotide encoding chimeric hepatitis B virus core antigen polypeptide include plasmid, virus, phage, cosmid and other vectors conventionally used in the art. Examples of the plasmid vector include, but are not limited to, pCAGGS (Gene 108: 193-199 (1991)), pCR-X8 (Vaccine 24: 4942-4950 (2006)), pcDNA3.1 (trade name, Invitrogen), pZeoSV (trade name, Invitrogen), pBK-CMV (trade name, Stratagene) and the like. The virus vector is a DNA virus or an RNA virus. Examples of the virus vector include, but are not limited to, detoxicated retrovirus, adenovirus, adeno-associated virus, herpes virus, vaccinia virus, poxvirus, polio virus, Sindbis virus, Hemagglutinating Virus of Japan (HVJ), SV40, human immunodeficiency virus (HIV) and the like. Furthermore, Hemagglutinating Virus of Japan envelope (HVJ-E) and the like can also be utilized.

In the above-mentioned expression vector, polynucleotide (preferably DNA) encoding chimeric hepatitis B virus core antigen polypeptide is operably connected to a promoter capable of exhibiting a promoter activity in the cell of a mammal (preferably human) to be the administration subject.

The promoter to be used is not particularly limited as long as it can function in the cell of a mammal (preferably human) to be the administration subject. Examples of the promoter include pol I promoter, pol II promoter, pol III promoter and the like. Specifically, virus promoters such as SV40-derived initial promoter, cytomegalovirus LTR and the like, mammal constituting protein gene promoters such as β-actin gene promoter and the like, RNA promoters such as tRNA promoter and the like, and the like are used.

The above-mentioned expression vector preferably contains a transcription termination signal, i.e., terminator region, at the downstream of the polynucleotide encoding chimeric hepatitis B virus core antigen polypeptide. It can further contain a selection marker gene for the selection of a transformed cell (gene conferring resistance to medicaments such as tetracycline, ampicillin, kanamycin and the like, gene complementing auxotrophic mutation etc.).

In one embodiment, the above-mentioned expression vector may contain an immune stimulatory sequence (ISS) (also referred to as CpG) to potentiate the immune effect. The immune stimulatory sequence is a DNA containing a non-methylated CpG motif of bacterium, and is known to function as a ligand of a particular receptor (Toll-like receptor 9) (see Biochim. Biophys. Acta 1489, 107-116 (1999) and Curr. Opin. Microbiol. 6, 472-477 (2003) for the detail). Preferable examples of the immune stimulatory sequence include the following.

```
CpG-B1018 22 bp
                                           (SEQ ID NO: 6)
5'-tga ctg tga acg ttc gag atg a-3'

CpG-A D19 20 bp (D type)
                                           (SEQ ID NO: 7)
5'-ggt gca tcg atg cag ggg gg-3'

CpG-CC274 21 bp
                                           (SEQ ID NO: 8)
5'-tcg tcg aac gtt cga gat gat-3'

CpG-CC695 25 bp
                                           (SEQ ID NO: 9)
5'-tcg aac gtt cga acg ttc gaa cgt t-3'
```

Alternatively, 2, 3 or 4 from these ISSs may be connected and used. Preferable examples of the connected ISS sequence include the following.
5'-ggt gca tcg atg cag ggg gg tga ctg tga acg ttc gag atg a tcg tcg aac gtt cgagat gat tcg aac gtt cga acg ttc gaa cgt t-3' (SEQ ID NO: 10)

Those of ordinary skill in the art can construct the aforementioned expression vector according to well-known genetic engineering techniques described in, for example, "edit. Sambrook et al., Molecular Cloning A Laboratory Manual Cold Spring Harbor Laboratory (1989) N.Y.", "edit. Ausubel et al., Current Protocols in Molecular Biology (1987) John Wiley & Sons" and the like.

The therapeutic or prophylactic agent of the present invention can be provided as a pharmaceutical composition containing, in addition to a therapeutically effective amount of the above-mentioned expression vector, any carrier, for example, a pharmaceutically acceptable carrier.

Examples of the pharmaceutically acceptable carrier include, though not limited thereto, excipients such as sucrose, starch, mannit, sorbit, lactose, glucose, cellulose, talc, calcium phosphate, calcium carbonate and the like, binders such as cellulose, methylcellulose, hydroxypropylcellulose, gelatin, gum arabic, polyethylene glycol, sucrose, starch and the like, disintegrants such as starch, carboxymethylcellulose, hydroxypropylstarch, sodium-glycol-starch, sodium hydrogen carbonate, calcium phosphate, calcium citrate and the like, lubricants such as magnesium stearate, aerosil, talc, sodium lauryl sulfate and the like, aromatics such as citric acid, menthol, glycyrrhizin.ammonium salt, glycine, orange power and the like, preservatives such as sodium benzoate, sodium bisulfite, methylparaben, propylparaben and the like, stabilizers such as citric acid, sodium citrate, acetic acid and the like, suspensions such as methylcellulose, polyvinylpyrrolidone, aluminum stearate and the like, dispersing agents such as surfactant and the like, diluents such as water, saline and the like, base waxes such as cacao butter, polyethylene glycol, white kerosine and the like, and the like.

The therapeutic or improving agent of the present invention may further contain an adjuvant to potentiate its effect. Examples of the adjuvant include aluminum hydroxide, complete Freund's adjuvant, incomplete Freund's adjuvant, pertussis adjuvant, poly(I:C), CpG-DNA and the like.

To promote intracellular introduction of an expression vector, the therapeutic or prophylactic agent of the present invention may further contain a reagent for nucleic acid introduction. As the reagent for nucleic acid introduction, cationic lipids such as lipofection (trade name, Invitrogen), lipofectamine (trade name, Invitrogen), transfectam (trade name, Promega), DOTAP (trade name, Roche Applied Science), dioctadecylamidoglycyl spermine (DOGS), L-dioleoyl phosphatidyl-ethanolamine (DOPE), dimethyldioctadecyl-ammonium bromide (DDAB), N,N-di-n-hexadecyl-N,N-dihydroxyethylammonium bromide (DHDEAB), N-n-hexadecyl-N,N-dihydroxyethylammonium bromide (HDEAB), polybrene, poly(ethyleneimine) (PEI) and the like can be used. In addition, an expression vector may be included in any known liposome constituted of a lipid bilayer such as electrostatic liposome. Such liposome may be fused with a virus such as inactivated Hemagglutinating Virus of Japan (HVJ). HVJ-liposome has a very high fusion activity with a cellular membrane, as compared to general liposomes. When retrovirus is used as an expression vector, RetroNectin, fibronectin, polybrene and the like can be used as transfection reagents.

While the content of the above-mentioned expression vector in the pharmaceutical composition is not particularly limited and appropriately selected from a wide range, it is generally about 0.00001 to 100 wt % of the whole pharmaceutical composition.

By introducing the above-mentioned expression vector into an application target, mammalian tissue (or cell), the therapeutic or prophylactic agent of the present invention induces an in vivo expression of the above-mentioned antigen polypeptide (e.g. chimeric hepatitis B virus core antigen polypeptide), induces production of an antibody to a specific epitope of apolipoprotein (a) contained in the antigen polypeptide, as a result of which the induced antibody suppresses production of lipoprotein (a), thereby suppressing neointimal formation and blood vessel intimal thickening. Various methods for introducing nucleic acids such as expression vector and the like into the body are known (T. Friedman, Science 244: 1275-1281 (1989)), and any introduction method can be employed as long as it induces an in vivo expression of the above-mentioned antigen polypeptide (e.g. chimeric hepatitis B virus core antigen polypeptide), induces production of an antibody to a specific epitope of apolipoprotein (a) contained in the antigen polypeptide, and treats or prevents lipoprotein (a)-related diseases including arteriosclerosis.

Examples of the method for introducing an expression vector into a mammalian tissue (or cell) in vivo include, but are not limited to, inner liposome method, electrostatic liposome method, HVJ-liposome method, HVJ-AVE liposome method, receptor-mediated transgene, particle gun method, naked DNA method, introduction method by positive electric charge polymer, electroporation method and the like.

Alternatively, cells such as blood cells, bone marrow cells and the like may be isolated from the application target mammal, the above-mentioned expression vector may be introduced into the cells ex vivo, after which cells containing the obtained above-mentioned expression vector may be returned to the application target mammal.

Examples of the method for introducing an expression vector into a mammalian cell ex vivo include, but are not limited to, lipofection method, calcium phosphate coprecipitation method, DEAE-dextran method, direct DNA introduction method using glass microcapillary, electroporation method and the like.

The therapeutic or prophylactic agent of the present invention may be administered by any method as long as in the administration subject mammal, the agent induces in vivo expression of the above-mentioned antigen polypeptide (e.g. chimeric hepatitis B virus core antigen polypeptide), induces production of an antibody to a specific epitope of apolipoprotein (a) contained in the antigen polypeptide (e.g. chimeric hepatitis B virus core antigen polypeptide), and treats or prevents lipoprotein (a)-related diseases including arteriosclerosis. Preferably, the therapeutic or prophylactic agent of the present invention is parenterally administered in an amount sufficient to induce production of an antibody to a specific epitope of apolipoprotein (a) contained in the antigen polypeptide (e.g. chimeric hepatitis B virus core antigen polypeptide), and treat or prevent lipoprotein (a)-related diseases including arteriosclerosis. For example, injection via intravenous, intraperitoneal, subcutaneous, intradermal, intraadipose tissue, intramammary gland tissue, or intramuscular pathway; gas induced particle bombarding method (by electron gun and the like); a method in the form of collunarium and the like via a mucosal pathway, and the like are recited as examples of the administration methods. In one embodiment, the therapeutic or prophylactic agent of the present invention is preferably injected subcutaneously or intramuscularly.

In one embodiment, the therapeutic or prophylactic agent of the present invention is subcutaneously administered by a needleless injector. The needleless injector is preferably a pressure injector. Examples of the needleless injector include, but are not limited to, ShimaJET (trade name, SHIMADZU CORPORATION), Twinject EZII (trade name, Japan chemical research), Syrijet (trade name, Keystone), ZENEO (trade name, Crossject) and the like. In this case, the therapeutic or prophylactic agent of the present invention can be provided as an injection preparation containing the above-mentioned expression vector and needleless injector, wherein the expression vector is enclosed in the needleless injector.

In one embodiment, the therapeutic or prophylactic agent of the present invention is administered subcutaneously, intradermally or intramuscularly with a gene gun. In this case, the above-mentioned expression vector may be applied onto the carrier particles such as colloidal gold particles and the like to be introduced into the body and used for administration. A technique for coating carrier particles with polynucleotide is known (see, for example, WO93/17706). Finally, the expression vector can be prepared in an aqueous solution such as physiological brine and the like suitable for administration to the body.

To induce good immune responses, the therapeutic or improving agent of the present invention is preferably administered plural times at given intervals. While the frequency can be appropriately determined by monitoring the level of immune response, it is generally 2-10 times, preferably 2-6 times, more preferably 2, 3 or 4 times.

The administration frequency is generally once per 1 week-1 year, preferably once per 1-6 months.

While the dose of the therapeutic or prophylactic agent of the present invention depends on the immunogenicity of a specific epitope of apolipoprotein (a) contained in the antigen polypeptide (e.g. chimeric hepatitis B virus core antigen polypeptide) encoded by the active ingredient expression vector in an administration subject mammal, those of ordinary skill in the art can determine the dose necessary for a good immune response by administering a given amount of an expression vector to an administration subject mammal, measuring the antibody titer specific to the epitope by a detection method such as ELISA and the like, and observing the immune response. Those of ordinary skill in the art appreciate that the immunogenicity of the therapeutic or prophylactic agent of the present invention also depends on the strength of the regulatory sequence such as promoter used for the expression vector as an active ingredient. Moreover, those of ordinary skill in the art can also control the dose of the therapeutic or prophylactic agent of the present invention with ease depending on the kind of the expression vector to be used.
an antigen polypeptide (e.g.
lipoprotein (a)-related diseases including When an expression vector encoding an antigen polypeptide (e.g. chimeric hepatitis B virus core antigen polypeptide) inserted with an amino acid sequence comprising a specific epitope of apolipoprotein (a) is administered, an immune reaction (preferably humoral immune reaction such as antibody production and the like) against the specific epitope of apolipoprotein (a) in the expressed antigen polypeptide (e.g. chimeric hepatitis B virus core antigen polypeptide) is induced, and production of lipoprotein (a) is suppressed by an antibody to apolipoprotein (a), whereby neointimal formation and vascular intimal thickening are suppressed. Therefore, an administration subject of the therapeutic or prophylactic agent of the present invention includes patients with a lipoprotein (a)-related disease (e.g. arteriosclerosis (preferably, atherosclerosis)), non-lipoprotein (a)-related disease patients with the risk of developing lipoprotein (a)-related disease (e.g. arteriosclerosis (preferably, atherosclerosis)) (e.g., healthy individual; individual who has not developed lipoprotein (a)-related disease (e.g. arteriosclerosis) while blood apolipoprotein (a) level or lipoprotein (a) level is higher than healthy individual; hyperlipidemia patients etc.) and the like. By administering an expression vector encoding an antigen polypeptide (e.g. chimeric hepatitis B virus core antigen polypeptide) inserted with an amino acid sequence comprising a specific epitope of apolipoprotein (a) to lipoprotein (a)-related disease (e.g. arteriosclerosis) patients, further deposition of lipoprotein (a) in the diseased part of the patients can be suppressed, neointimal formation and vascular intimal thickening can be suppressed, whereby the progression of lipoprotein (a)-related disease (e.g. arteriosclerosis) can be inhibited. In addition, by administering an expression vector encoding an antigen polypeptide (e.g. chimeric hepatitis B virus core antigen polypeptide) inserted with an amino acid sequence comprising a specific epitope of apolipoprotein (a) to non-lipoprotein (a)-related disease patients (e.g. non-arteriosclerosis patients) with the risk of developing lipoprotein (a)-related disease (e.g. arteriosclerosis), the onset of lipoprotein (a)-related disease (e.g. arteriosclerosis) in the non-lipoprotein (a)-related disease patients (e.g. non-arteriosclerosis patients) can be prevented.

All references cited in the present specification, including publication, patent document and the like, are hereby incorporated individually and specifically by reference, to the extent that the entireties thereof have been specifically disclosed herein.

The present invention is explained in more detail in the following by referring to Examples, which are not to be construed as limitative.

EXAMPLES

Example 1

[Materials and Methods]
Animals

The experiments were approved by the Ethical Committee for animal experiments of Osaka University Graduate School of Medicine. Mice had free access to water and food during the experimental periods. Female FVB mice were purchased from Charles River. Lp(a) transgenic mice were created by the mating of human apo(a) transgenic mice and human apoB transgenic mice (Nature genetics, 1995, 9: 424-431; Nature, 1992, 360: 670-672; Proceedings of the National Academy of Sciences, 1994, 91: 2130; Circulation, 2002, 105: 1491-1496). Human apo(a) YAC transgenic mice were created by insertion of human apo(a) YAC transgenic mice, including the apo(a) gene, 70 kb apo(a)-like gene, and the 260 kb genomic DNA (YAC DNA) (Nature, 1992, 360: 670-672). Human apoB transgenic mice were created by insertion of 76 kb genomic DNA (P1 phagemid DNA) containing the intact apoB gene (Proceedings of the National Academy of Sciences, 1994, 91: 2130). The background of both mice was FVB mouse.

Construction of HBc-apo(a) Fusion Gene Expression Vector

The plasmid pcDNA3.1 (pcDNA3.1/V5-His-TOPO, Invitrogen) containing the cytomegalovirus promoter was used. The HBc gene was obtained by PCR and engineered into pcDNA3.1 [HBc]. The apo(a) 12 amino acids (a.a.) sequence (EAPSEQAPTEQR: SEQ No. 1) with a N-terminus Ile-Thr dipeptide linker and C-terminus Gly-Ala-Thr tripeptide extension was synthesized by PCR using the following oligonucleotide:
(PCR1)

```
the forward primer: HBc-1
                                          (SEQ ID NO: 11)
5'GCCATGGATATCGATCCTTATAAAGAATTCGGAGC3', the reverse primer: Lp(a)-1
                                          (SEQ ID NO: 12)
5' GTTAACTTGGAAGATCCAGCTATCACTGAGGCTCCTTCCGAACAA
GCACCGACT3',
and
```

```
template: pPLc3 (BCCM/LMBP);

(PCR2)
the forward primer: HBc-2
                                              (SEQ ID NO: 13)
5'GGCCTCTCACTAACATTGAGATTCCCGAGATTGAGA3', the reverse primer: Lp(a)-2
                                              (SEQ ID NO: 14)
5'TTCCGAACAAGCACCGACTGAGCAAAGGGGTGCTACTAGCAGGGACC
TGGTAGTC3',
and template: pPLc3
```

The PCR products from PCR1 and PCR2 were use as the template of PCR3. In PCR3, HBc-1 was used as the forward primer and HBc-2 was used as the reverse primer. The PCR product from PCR3 was engineered into pcDNA3.1 [HBc-apo(a)].

Vaccination Protocol

Female FVB or Lp(a) transgenic mice were vaccinated intramuscularly three times at 2-week interval (8 weeks, 10 weeks, 12 weeks old, respectively) with 60 µL TE containing 120 µg HBc-apo(a) or HBc, or 60 µL saline. In the vaccination, electric pulse generator (NEPA GENE) connected to a switch box with a pair of stainless steel needles of 10 mm in length and 0.3 mm in diameter, fixed with a distance between them of 3 mm was used. The voltage remained constant, 70V, during the pulse duration. Three pulses of the indicated voltage followed by three more pulses of the opposite polarity were administered to each injection site at a rate of one pulse/s, with each pulse being 50 ms in duration. Six weeks after third immunization (18 weeks old), additional immunization was given to mice. Lp(a) transgenic mice were bilateral ovariectomized before first immunization.

Measurement of Apo(a) Antibody in Serum

Two weeks after both third immunization and last immunization, respectively, serum was collected from immunized mice of all groups. Serum levels of apo(a)-specific antibodies in these mice were measured by ELISA. Briefly, ELISA plates was coated with 5 µg/mL apo(a) 12 a.a. peptide (peptide consisting of the amino acid sequence shown by SEQ ID NO: 1) in carbonate buffer overnight at 4° C. The plates were blocked with PBST containing 3% skim milk at room temperature for 2 hours, and serial dilution (1:100 to 1:312500) of serum samples from immunized mice were added to the well. Further, the plates were incubated overnight at 4° C., washed seven times with PBST, and HRP-conjugated mouse IgG (whole or each subtype) was added and incubated at room temperature for three hours. After four times wash with PBST, 3, 3', 5, 5'-tetramethylbenzidine (TMB, Sigma-Aldrich) was added, the blue reaction product was stopped by 0.5 mol/L sulfuric acid and the resulting end product was read at 450 nm.

T-Cell Proliferation Assay

The T-cell proliferation assay was performed as previously reported. Syngeneic T-cells (mouse splenocytes, $5 \times 10^5$ cells/well) were cultured with 10 µg/ml recombinant apo(a) 12 a.a. peptide, phytohemagglutinin (PHA, 50 µg/mL as positive control) and medium separately, at 37° C., 5% $CO_2$ for 40 hours. Further, 1 µCi of [$^3$H] thymidine (Perkin Elmer) was added to each well for 8 hours. The cells were harvested, and the [$^3$H] thymidine uptake was determined using a MicroBeta 1450 Trilux scintillation counter (Wallac Oy). The stimulation index was expressed as the ratio of stimulated cells to non-stimulated cells.

Enzyme-Linked ImmunoSpot (ELISpot) Assay

ELISpot assay was carried out using Mouse IFN-γ Development Module and Mouse IL-4 Development Module, respectively (R&D Systems) according to the manufacturer's instructions. Briefly, 96-well filter plates for ELISpot were preincubated with anti-mouse IFN-γ or IL-4 antibodies overnight at 4° C. and blocked with PBS containing 1% BSA and 5% sucrose. For two hours at room temperature. The splenocytes from individual immunized mice of $5 \times 10^5$ cells per well were added to wells with 10 µg/ml recombinant apo(a) 12a.a. peptide, PHA (50 µg/mL as positive control) and medium separately, and incubated at 37° C., 5% $CO_2$ for 48 h. The plates were washed four times with PBST, incubated with biotinylated anti-mouse IFN-γ or IL-4 antibody overnight at 4° C. and washed again with PBST three times. ELISpot color module (R&D systems) was used as color development. Diluted Streptavidin-AP concentrate with PBS containing 1% BSA complex was added into each well and incubated for 2 hours at room temperature. After washing with PBS-T and deionized water, BCIP/NBT was added into each well and incubated in dark for 30 minutes at room temperature. The plates were washed with deionized water, air-dried at room temperature. The colored spots were quantified manually using a dissecting microscope (Olympus).

Carotid Artery Ligation Model

Carotid artery ligation model was performed for Lp(a) female transgenic mice as previously described. One week after the final immunization, the left common carotid artery of female Lp(a) transgenic mice was exposed through a small midline incision in the neck, and the artery was completely ligated with a 6-0 silk just proximal to the carotid bifurcation to disrupt blood flow. Following ligation of the common carotid artery, the vessel typically undergoes inflammatory changes and neointima formation.

Pathological Analysis

Quantification of vascular remodeling was performed after three weeks of carotid ligation model. The left common carotid artery was removed and fixed in 4% paraformaldehyde, equilibrated in PBS containing 10% sucrose, in PBS/20% sucrose and in PBS/30% sucrose. The samples were then embedded for quick freezing. Cross sections were laid on slides and stained; some of them were frozen at −80° C. For evaluation of neointima formation, slides were stained with hematoxylin and eosin (HE). Each five stained slide was quantified by measuring the area of neointima and media (Image J). Immunostaining with anti-Lp(a) antibody were visualized with VECTASTAIN ABC-AP and Vector Red (Vector Laboratories Inc.).

Statistics

All values were expressed as mean±S.E.M. Data were compared by t-test or using ANOVA followed by Fischer's test for multiple comparisons. All statistical analysis was performed using StatView (SAS Institute, Inc.). Values of $p<0.05$ were considered to represent statistical significance.

[Results]

In Vitro Expression of Plasmid DNA Construct

Plasmid DNA including hepatitis B virus cores protein (HBc) was used because HBc is a carrier protein and possesses its ability to self-assemble into icosahedral virus-like particles (VLPs) in heterologous expression systems. The plasmid pcDNA3.1-HBc (control vector) and pcDNA3.1-HBc-apo(a) were constructed (FIG. 1a). The 12 amino acids (EAPSEQAPTEQR: SEQ No. 1) of apo(a) were selected as a targeted antigen, which is overlapped in repeated sequences of kringle-4 type 2 of apo(a) and multiply presented in the repeated kringle IV domain type2 domain. (FIGS. 1b and 1c). Although apo(a) is a high homologue of plasminogen, containing multiple copies of kringle-4, a single copy of kringle-5 and an inactive protease domain, the selected epitope sequence was not high homology with plasminogen. The antigen sequence was hydrophilic domain and known as a potential of B-cell epitope as previously described (Clinica chimica acta, 1999, 287: 29-43).

DNA Vaccination to FVB Mice

Figure 2:
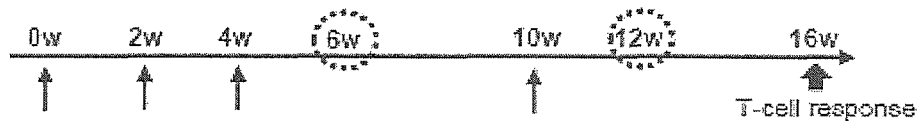
FIG. 2 shows DNA vaccination for Apo(a) to FVB mice. a) Time course of DNA vaccination. Vaccination was done at 8 weeks old (0 W) and at 2 weeks (2 W), 4 weeks (4 W), 10 weeks (10 W) after first vaccination. Titer was quantified at 6 weeks and 12 weeks after first vaccination, and T cell activity was evaluated at 16 weeks after first vaccination. b) and c) Titer of anti-apo(a) antibodies at 6 weeks and 12 weeks. Total IgG titer for apo(a) was increased only in mice serum (×100 dilution) from HBc-apo(a) group (left panel). IgG subtype (IgG1, IgG2a or IgG2b) in mice serum (×100 dilution) from HBc-apo(a) group was also evaluated by each IgG specific antibody (right panel). d) Anti-plasminogen antibodies in mice assayed by ELISA. Total IgG titer for plasminogen were evaluated in mice serum (×100 dilution) from HBc-apo(a) group at 6 week and 12 weeks after first immunization and anti-plasminogen antibody (PLG Ab) was used as a positive control.
Figure 2:
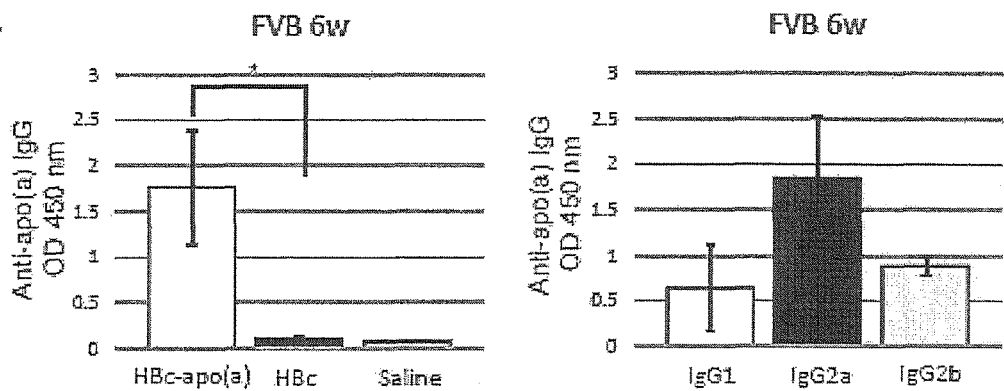
Figure 2:
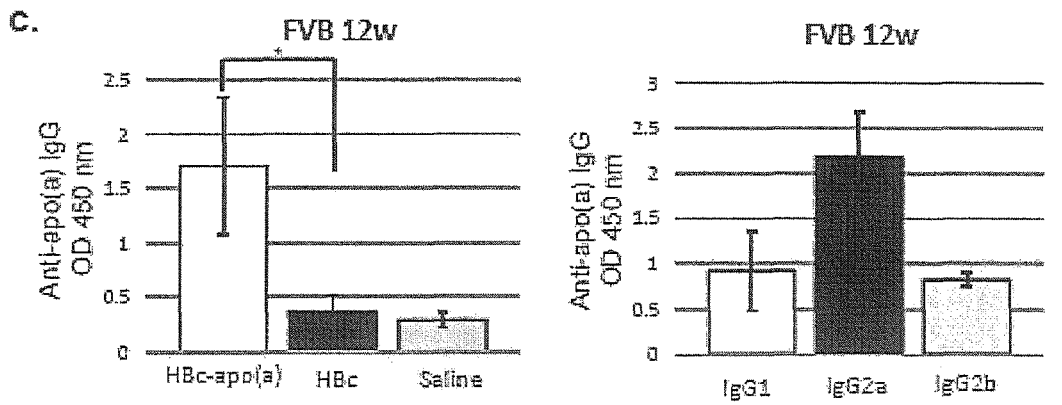
Figure 2:
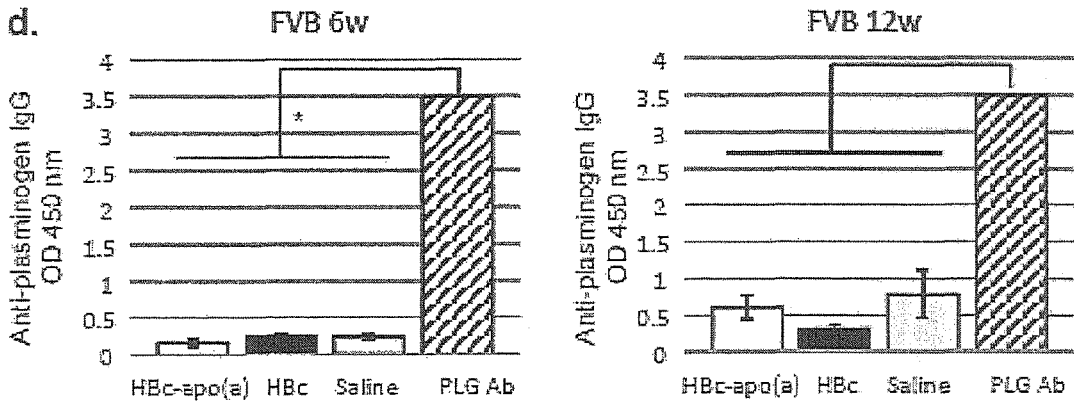

FVB female mice were immunized with pcDNA3.1-HBc-apo(a) [HBc-apo(a)], pcDNA3.1-HBc [HBc] or saline, respectively, by intramuscular administration using electroporator, three times every two weeks (FIG. 2a). Although FVB has no endogenous apo(a), the antigen of this DNA vaccine might be recognized as a foreign substance. Titer of anti-apo(a) antibody was observed only in HBc-apo(a) group (FIG. 2b—left). From the analysis of IgG subtypes, the immunization was predicted to lead to Th1-biased immune responses with predominant IgG2a production (FIG. 2b—right). Six weeks after third immunization, additional immunization was given to mice, which raised the titer of anti-apo(a) antibody (FIG. 2c—left). This immunization was also predicted to lead to Th1-biased immune responses with predominant IgG2a production (FIG. 2c—right). Furthermore, anti-plasminogen antibodies were not detected after these immunization (FIG. 2d), although apo(a) was highly homologue to plasminogen, which indicated that these immunization had little effect on fibrinolytic system.

Figure 3:
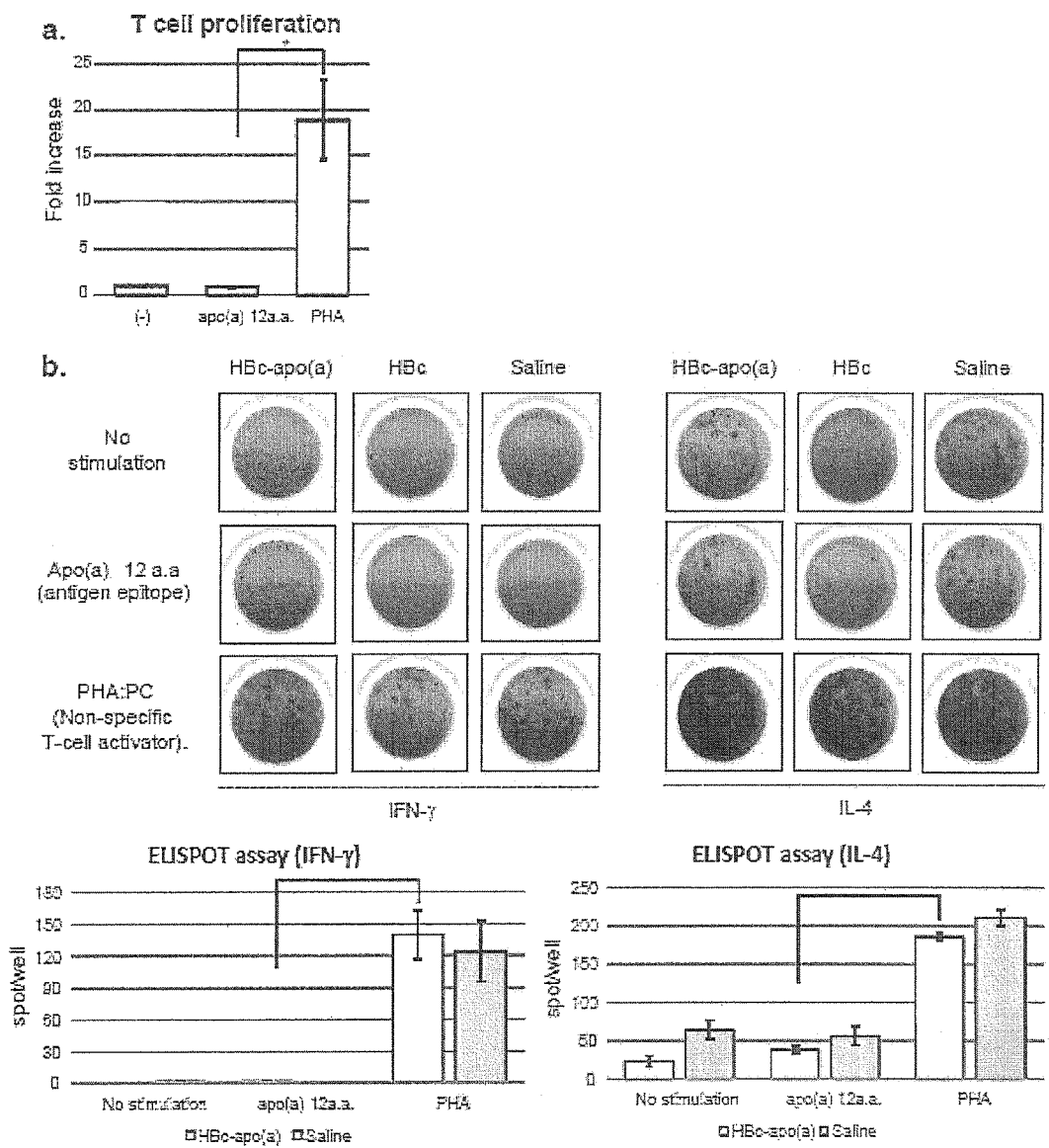
FIG. 3 shows T-cell responses induced by DNA vaccination in FVB mice. a) T-cell proliferation assay by [$^3$H] thymidine uptake. Cultured splenocytes from mice immunized with HBc-apo(a) were stimulated with or without peptide consisting of antigen sequence (apo(a) 12a.a.; EAPSEQAPTEQR: SEQ ID NO: 1). PHA was used as positive control of non-specific T-cell activator. b) Enzyme-Linked ImmunoSpot (ELISpot) assay. Splenocytes obtained from mice immunized with HBc-apo(a), HBc or Saline were stimulated with or without the antigen sequence peptide or PHA. Blue dots are positive spots for IFN-gamma (left panel) and IL-4 (right panel). c) Quantification of ELISpot assay. Quantification was assessed by counting spot numbers per well in each well.

To assess the safety and validity of the epitope, 12 a.a in apo(a), T-cell proliferation assay and ELISpot assay were performed. In immunized female FVB mice, T-cell proliferation assay showed that stimulation with apo(a) 12 a.a. peptide (peptide consisting of the amino acid sequence shown by SEQ ID NO: 1) did not induce the proliferation of splenocytes from immunized mice (FIG. 3a). Also, in ELISpot assay, stimulation with apo(a) 12 a.a. peptide induced a production of neither IFN-γ nor IL-4 (FIGS. 3b and 3c). These data indicated that the amino acid sequence shown by SEQ ID NO: 1 did not contain T-cell epitopes to induce T-cell activation.

DNA Vaccination to Lp(a) Transgenic Mice

Figure 4:
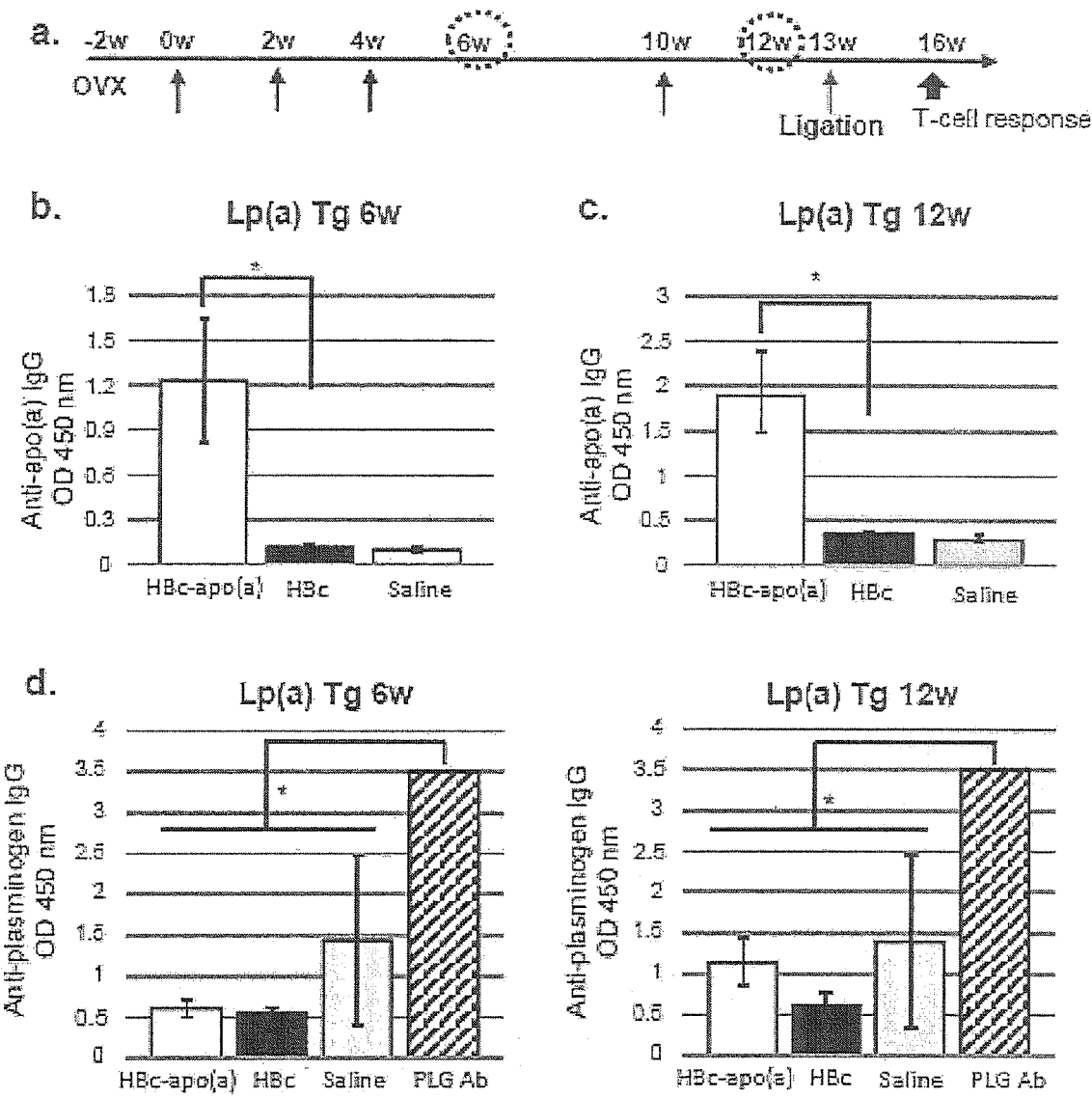
FIG. 4 shows DNA vaccination for apo(a) in Lp(a) transgenic mice. a) Time course of DNA vaccination. Female Lp(a) transgenic mice were ovariectomized at 8 weeks old. After 2 weeks, DNA vaccination was done at 10 weeks old (0 W) and at 2 weeks (2 W), 4 weeks (4 W), and 10 weeks (10 W) after first vaccination. Titer was quantified at 6 weeks and 12 weeks after first vaccination, and T cell activity was evaluated at 16 weeks after first vaccination. b and c) Total IgG titer for apo(a) was increased only in mice serum (×100 dilution) from HBc-apo(a) group. d) Anti-plasminogen antibodies in mice assayed by ELISA. Total IgG titer for plasminogen were evaluated in mice serum (×100 dilution) from HBc-apo(a) group at 6 week and 12 weeks after first immunization and anti-plasminogen antibody (PLG Ab) was used as a positive control.

As apo(a) is present only in humans, primates and hedgehogs, Lp(a) transgenic mice generated by crossing human apo(a) transgenic mice and human apoB transgenic mice were used (Nature genetics, 1995, 9: 424-431; Nature, 1992, 360: 670-672; Proceedings of the National Academy of Sciences, 1994, 91: 2130; Circulation, 2002, 105: 1491-1496). In Lp(a) transgenic mice, serum Lp(a) level was higher in female mice than in male mice (Atherosclerosis, 211: 41-47). Since the bilateral ovariectomy in Lp(a) transgenic mice increased serum Lp(a) level, ovariectomy on Lp(a) transgenic mice was performed two weeks before first immunization. Similarly, Lp(a) transgenic mice were immunized (FIG. 4a). Two weeks after third and fourth immunization, titer of anti-apo(a) antibody was observed only in HBc-apo(a) group (FIGS. 4b and 4c). In Lp(a) transgenic mice, this immunization also did not produce anti-plasminogen antibodies (FIG. 4d).

As to DNA vaccination to Lp(a) transgenic mice, T-cell proliferation assay and ELISpot assay were performed. In immunized Lp(a) transgenic mice, T-cell proliferation assay showed that stimulation with apo(a) 12 a.a. peptide did not induce the proliferation of splenocytes from immunized mice. In ELISpot assay, stimulation with apo(a) 12 a.a. peptide induced a production of neither IFN-γ nor IL-4. These data also indicated that the amino acid sequence shown by SEQ ID NO: 1 did not contain T-cell epitopes to induce T-cell activation.

Carotid Artery Ligation Model in Lp(a) Transgenic Mice

Figure 5:
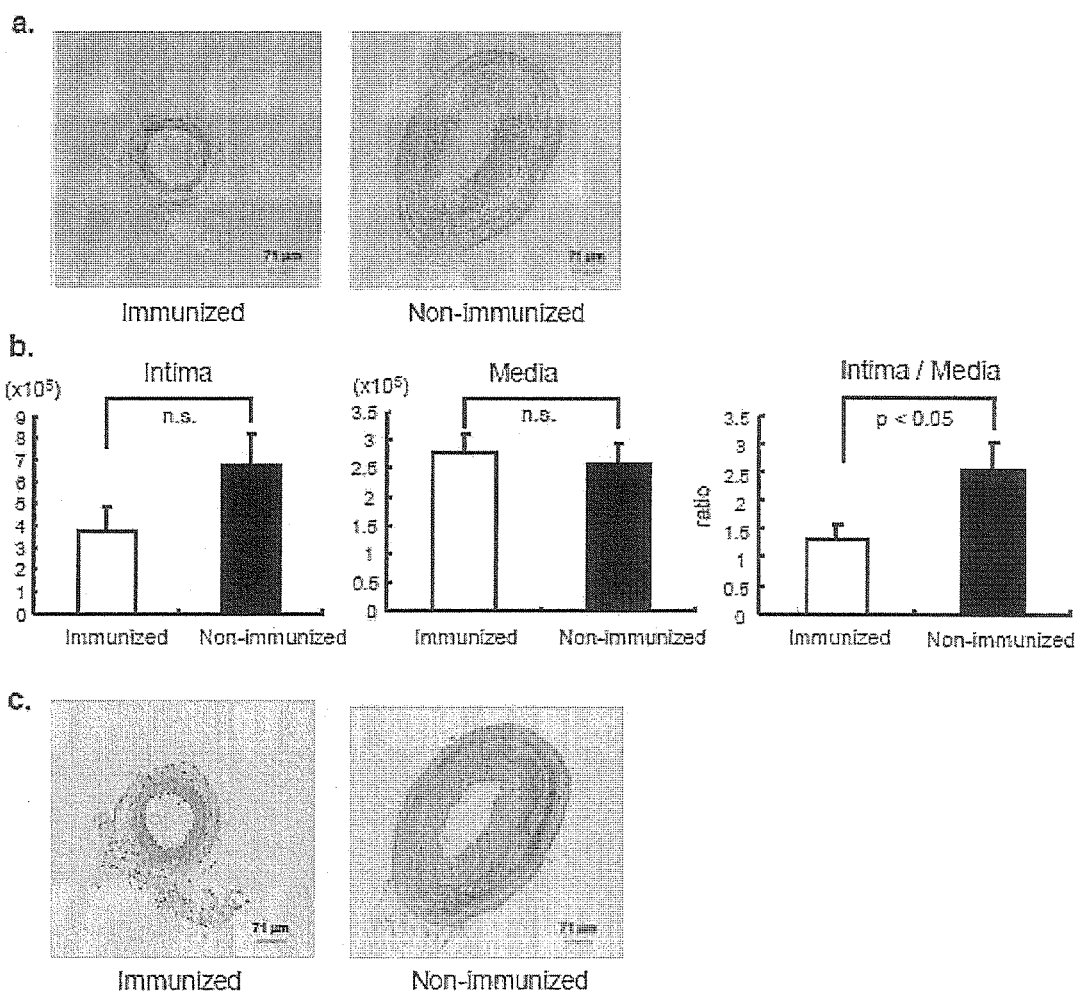
FIG. 5 shows carotid artery ligation model in Lp(a) transgenic mice. a) Representative images of H&E staining in ligated vessels. Left panel shows the immunized mice (HBc-apo(a) group) and Right panel shows the non-immunized mice (saline and HBc). Carotid artery ligation was performed at 13 weeks after first immunization, and the vascular remodeling was evaluated at 16 weeks. b) Quantification of intima and media area and ratio of intima to media in immunized mice and non-immunized mice. c) Immunostaining with anti-Lp(a) antibody. Lp(a) deposition (pink) in ligated vessels was observed only in non-immunized group.

As a result of flow cessation caused by ligation of the left common carotid artery, a higher increase in intima formation was observed in Lp(a) transgenic mice immunized with HBc and saline, compared to Lp(a) transgenic mice immunized with HBc-apo(a) (FIG. 5a). There was no difference in media formation among Lp(a) transgenic mice immunized HBc-apo(a), HBc or saline. The ratio of intima to media was higher significantly in HBc and saline group than HBc-apo (a) group (FIG. 5b), suggested that HBc-apo(a) vaccination to Lp(a) transgenic mice attenuated neointima formation (FIG. 5b). Moreover, the expression of Lp(a) in ligated vessels of Lp(a) transgenic mice was assessed by immunohistochemistry. There are multiple studies documenting the deposition of Lp(a) in arteries affected by atherosclerosis. The deposition of Lp(a) in ligated vessels was observed in non-immunized group much more strongly than in immunized group (FIG. 5c). Unexpectedly, HBc-apo(a) vaccination did not decrease serum Lp(a) level.

The produced amino acid sequence of HBc-apo(a) is shown in SEQ ID NO: 16, and the nucleotide sequence encoding the amino acid sequence is shown in SEQ ID NO: 15. The following region corresponds to the inserted sequence.

nucleotide Nos. 244-294 of SEQ ID NO: 15 (Of these, nucleotide No. 250-285 encode SEQ ID NO: 1)
amino acid Nos. 81-97 of SEQ ID NO: 16 (Of these, amino acid Nos. 83-94 correspond to SEQ ID NO: 1)

Example 2

Carotid artery ligation model in Lp(a) transgenic mice in Example 1 was further analyzed.

Figure 6:
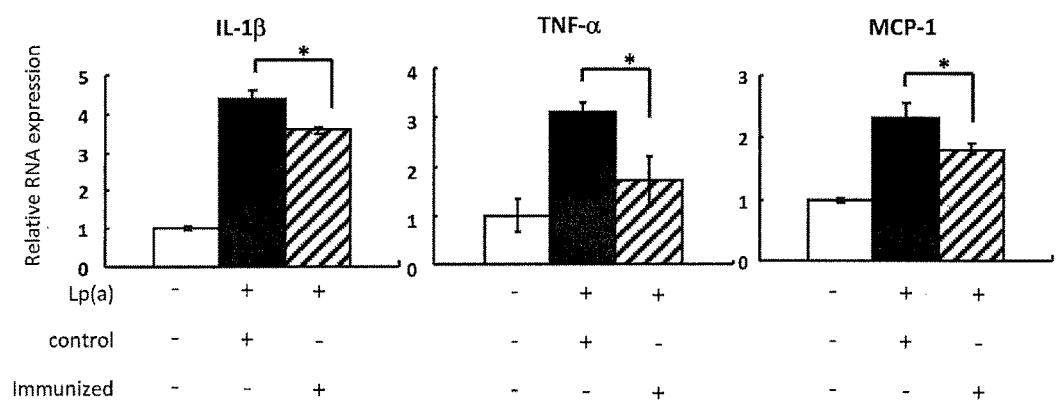
FIG. 6 shows the expression of the inflammatory cytokines (IL-1β, TNF-α, MCP-1) analyzed by real-time PCR, in macrophages that had differentiated from THP-1 cells in the presence of sera from mice immunized with HBc-apo(a) vaccine or control mice.
Figure 7:
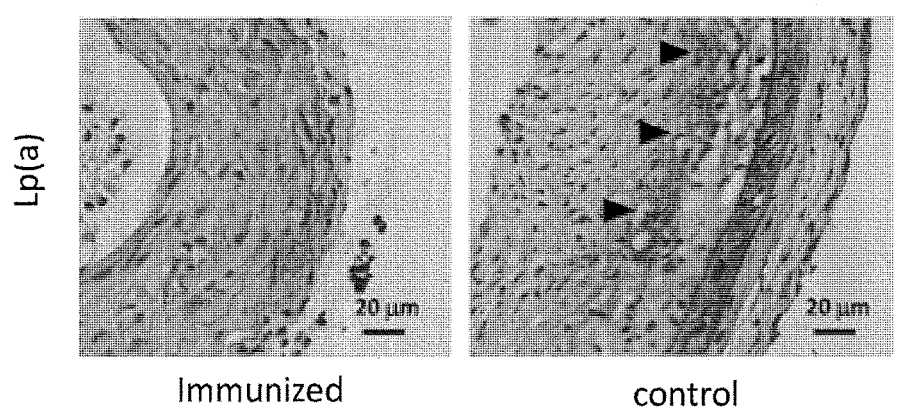
FIG. 7 shows Immunostaining of blood vessel with anti-Lp(a) antibody. Lp(a) deposition (pink, allow head) in ligated vessels was observed only in non-immunized group.

In order to evaluate neutralization activity of the antibody induced by HBc-apo(a) vaccination, expression of inflammatory cytokines (IL-1β, TNF-α, MCP-1) induced by Lp(a) was analyzed using real-time PCR in macrophages differentiated from THP-1 cells in the presence of sera from immunized (apo(a) vaccination) or control group mice. As a result, serum from mice vaccinated by HBc-apo(a) significantly inhibit LP(a) induced IL-1β, TNF-α, and MCP-1 expression in macrophase as compared to control mice serum (FIG. 6). This result suggests that HBc-apo(a) vaccination induces neutralizing antibody against apo(a), and the neutralizing antibody binds to Lp(a) in a blood to suppress inflammatory cytokine production due to Lp(a) stimulation, decreases the amount of inflammatory cytokine in the blood, thereby suppressing intimal thickening (i.e. arteriosclerosis).

In addition, Lp(a) deposition in ligated vessels in Lp(a) transgenic mouse was evaluated by immunohistochemistry. In control mice, Lp(a) deposition was localized to the site of arteriosclerosis disease (i.e. neointimal formation site). Such Lp(a) deposition was significantly decreased in mice immunized with HBc-apo(a) vaccine as compared to non-immunized group. These results suggest that neutralizing antibody against apo(a) induced by HBc-apo(a) vaccination binds to Lp(a) in a blood, and inhibits Lp(a) deposition to vascular tissue, thereby suppressing neointimal thickening (i.e. arteriosclerosis).

INDUSTRIAL APPLICABILITY

The present invention provides a DNA vaccine capable of treating or preventing arteriosclerosis, while avoiding self-reactive T cell induction.

The invention claimed is:

1. A method for treating (i) arteriosclerosis or (ii) a disease caused by arteriosclerosis, which disease is selected from a group consisting of cerebral infarction, myocardial infarction, angina, sclerosis obliterans, vascular dementia, and vascular restenosis, said method comprising:
administering to the mammal an effective amount of an expression vector encoding a chimeric hepatitis B virus core antigen polypeptide,
wherein the antigen polypeptide comprises the amino acid sequence of SEQ ID NO: 1 and the amino acid sequence of SEQ ID NO: 1
is inserted between amino acid residues 80 and 81 of the hepatitis B virus core antigen polypeptide,
wherein expression of the expression vector results in a decrease in lipoprotein (a) deposition and suppresses neointimal thickening, thereby treating (i) arteriosclerosis or (ii) the disease caused by arteriosclerosis, which disease is selected from a group consisting of cerebral infarction, myocardial infarction, angina, sclerosis obliterans, vascular dementia, and vascular restenosis, in the mammal.

2. The method according to claim 1, wherein a neutralizing antibody against lipoprotein(a) is produced by administering the expression vector.

3. The method according to claim 2, wherein the neutralizing antibody suppresses deposition of lipoprotein(a) to a vascular tissue.

4. The method according to claim 2, wherein the neutralizing antibody decreases the amount of an inflammatory cytokine in a blood.

5. The method according to claim 3, wherein arteriosclerosis is treated in the mammal.

6. The method according to claim 4, wherein arteriosclerosis is treated in the mammal.

7. The method according to claim 1, wherein arteriosclerosis is treated in the mammal.

8. The method according to claim 7, wherein the arteriosclerosis is atherosclerosis.

9. The method according to claim 1, wherein one or more specific epitopes in addition to the amino acid sequence of SEQ ID NO: 1 are inserted between amino acid residues 80 and 81 of the hepatitis B virus core antigen polypeptide.

10. The method according to claim 9, wherein the one or more specific epitopes comprise a specific epitope of apolipoprotein B.

11. The method according to claim 1, wherein the expression vector is administered multiple times.

12. The method according to claim 11, wherein the expression vector is administered 2, 3 or 4 times.

13. A method of inducing a neutralizing antibody against lipoprotein(a) in a mammal, comprising:
administering an effective amount of an expression vector encoding a chimeric hepatitis B virus core antigen polypeptide to a mammal,
wherein the antigen polypeptide comprises an amino acid sequence encoded by SEQ ID NO: 1 and the amino acid sequence encoded by SEQ ID NO: 1
is inserted between amino acid residues 80 and 81 of the hepatitis B virus core antigen polypeptide, and
wherein expression of the vector induces a neutralizing antibody against lipoprotein (a) in the mammal.

14. A method of treating arteriosclerosis in a mammal, comprising:
administering an effective amount of an expression vector to a mammal with arteriosclerosis,
wherein the expression vector encodes a chimeric hepatitis B virus core antigen polypeptide,
wherein the antigen polypeptide comprises an amino acid sequence encoded by SEQ ID NO: 1 and the amino acid sequence encoded by SEQ ID NO: 1
is inserted between amino acid residues 80 and 81 of the hepatitis B virus core antigen polypeptide, and
wherein the expression of the antigen polypeptide results in a decrease in lipoprotein (a) deposition and suppresses neointimal thickening, thereby treating arteriosclerosis in the mammal.

15. The method according to claim 14, wherein the arteriosclerosis is atherosclerosis.

16. The method according to claim 14, wherein one or more specific epitopes in addition to the amino acid sequence of SEQ ID NO: 1 are inserted between amino acid residues 80 and 81 of the hepatitis B virus core antigen polypeptide.

17. The method according to claim 16, wherein the one or more specific epitopes comprise a specific epitope of apolipoprotein B.

18. The method according to claim 14, wherein the expression vector is administered 2, 3 or 4 times.

19. A method for decreasing lipoprotein (a) deposition and/or neointima formation in a mammal, comprising:
administering an effective amount of an expression vector encoding a chimeric hepatitis B virus core antigen polypeptide to a mammal,
wherein the antigen polypeptide comprises an amino acid sequence encoded by SEQ ID NO: 1 and the amino acid sequence encoded by SEQ ID NO: 1
is inserted between amino acid residues 80 and 81 of the hepatitis B virus core antigen polypeptide, and
wherein the mammal has (i) arteriosclerosis or (ii) a disease caused by arteriosclerosis, which disease is selected from a group consisting of cerebral infarction myocardial infarction angina sclerosis obliterans vascular dementia and vascular restenosis,
thereby decreasing lipoprotein (a) deposition and/or neointima formation in the mammal.

20. The method according to claim 19, wherein one or more specific epitopes in addition to the amino acid sequence of SEQ ID NO: 1 are inserted between amino acid residues 80 and 81 of the hepatitis B virus core antigen polypeptide.

21. The method according to claim 20, wherein the one or more specific epitopes comprise a specific epitope of apolipoprotein B.

22. The method according to claim 19, wherein the expression vector is administered 2, 3 or 4 times.

* * * * *